United States Patent [19]
Li

[11] Patent Number: 6,014,214
[45] Date of Patent: Jan. 11, 2000

[54] HIGH SPEED INSPECTION OF A SAMPLE USING COHERENCE PROCESSING OF SCATTERED SUPERBROAD RADIATION

[76] Inventor: Ming-Chiang Li, 11415 Bayard Dr., Mitchellville, Md. 20721

[21] Appl. No.: 08/915,673

[22] Filed: Aug. 21, 1997

[51] Int. Cl.[7] ...................................................... G01B 9/02
[52] U.S. Cl. ............................................ 356/345; 356/359
[58] Field of Search ..................................... 356/345, 349, 356/357, 359, 360

[56] References Cited

U.S. PATENT DOCUMENTS

| | | | |
|---|---|---|---|
| 4,340,306 | 7/1982 | Balasubramanian | 356/360 |
| 4,928,005 | 5/1990 | Lefevre et al. | 250/227.23 |
| 5,317,369 | 5/1994 | Hochberg et al. | 356/359 |
| 5,321,501 | 6/1994 | Swanson et al. | 356/345 |
| 5,579,112 | 11/1996 | Sugiyama et al. | 356/360 |

FOREIGN PATENT DOCUMENTS 9219930   11/1992   WIPO .

OTHER PUBLICATIONS

High resolution optical ranging system by H. Park, M. Chodorow, and R. Kompfner, *Applied Optics*, vol. 20, No. 14, Jul. 15, 1981, pp. 2389–2394.

Waveguide optical switch in InGaAsP/InP using free–carrier plasma dispersion by O. Mikami and H. Nakagone, *Electron. Lett.*, vol. 20, No. 6, Mar. 1984, p. 228.

Optical coherence–domain reflectometry: a new optical evaluation technique by R.C. Youngquist, S. Carr, and D.E.N. Davies, *Optics Letters*, vol. 12, No. 3, Mar. 1987, pp. 158–160.

New measurement system for fault location in optical waveguide devices based on an interferometric technique by K. Takada, I. Yokohama, K. Chida, and J. Noda, *Applied Optics*, vol. 26, No. 9, May 1, 1987, pp. 1603–1606.

Guided–wave reflectometry with micrometer resolution by B.L. Danielson and C.D. Whittenberg, *Applied Optics*, vol. 26, No. 14, Jul. 15, 1987, pp. 2836–2842.

Eye–length measurement by interferometry with partially coherent light by A.F. Fercher, K. Mengedoht, and W. Werner, *Optics Letters*, vol. 13, No. 3, Mar., 1988, pp. 186–188.

Optical Reflectometry with Micrometer Resolution for the Investigation of Integrated Optical Devices by P. Beaud, J. Schütz, W. Hodel, H.P. Weber, H.H. Gilgen and R.P. Salthé, *IEEE J. Quantum Electronics*, vol. 25, No. 4, Apr. 1989, pp. 755–759.

Submillimeter Optical Reflectometry by H.H. Gilgen, R.P. Novak, R.P. Salathe, W. Hodel and P. Beaud, *J. of Lightwave Technology*, vol. 7, No. 8, Aug. 1989, pp. 1225–1233.

Interferometry and Synthesis in Radio Astronomy, by A.R. Thompson, J.M. Moran and G.W. Swenson, Jr. Krieger Publishing Company, Malabar, Florida 1991.

(List continued on next page.)

*Primary Examiner*—Samuel A. Turner

[57] ABSTRACT

Embodiments of the present invention are inspection methods and inspection apparatus for high speed, high precision inspection using parallel processing. In particular, an embodiment of a first aspect of the present invention is an inspection apparatus for inspecting a sample that uses parallel processing and which comprises: (a) a source of radiation which outputs superbroad inspection radiation having a frequency spectrum with an inspection width and reference radiation; (b) an inspection applicator apparatus which applies the inspection radiation as input to the sample; (c) an inspection collector apparatus which collects at least a portion of the inspection radiation that is scattered by the sample and applies at least a portion of the scattered inspection radiation as input to a dispersal apparatus; (d) wherein the dispersal apparatus applies radiation from the scattered inspection radiation as input to a plurality of coherence processors and applies radiation from the reference radiation as input to the plurality of coherence processors; and (e) a processor that fourier analyzes outputs from the coherence processors.

19 Claims, 21 Drawing Sheets

OTHER PUBLICATIONS

Practical Phased–Array Antenna Systems, Eli Brookner Editor, Artech House, Boston, pp. 2–27 to 2–40.

Water Penetration Sensing Using Wavelength Tunable OTDR by M. Tateda, *IEEE Photonics Tech Lett.*, vol. 3, No. 1, Jan. 1991, pp. 1–3.

Micron–Resolution Ranging of Cornea Anterior Chamber by Optical Reflectometry by D. Huang, J. Wang, C.P. Lin, C.A. Puliafito, and J.G. Fujimoto, *Lasers in Surg. and Med.*, vol. 11, 1991, pp. 419–425.

Polarization–Independent Interferometric Optical–Time Domain Reflectometer by M. Kobayashi, H. Hanafusa, K. Takada, and J. Noda, *J. Of Lightwave Technology*, vol. 9, No. 5, May 1991, pp. 623–628.

Optical Fiber Component Characterization by High–Intensity and High–Spatial–Resolution Interferometric Optical–Time–Domain Reflectometer by M. Kobayashi, H.F. Taylor, K. Takada, and J. Noda, *IEEE Photonics Technology Letters*, vol. 3, No. 6, Jun. 1991, pp. 564–566.

Rayleigh backscattering measurement of single–mode fibers by low coherence optical time–domain reflectometer with 14 $\mu$m spatial resolution by K. Takada and K–i Yukimatsu, *Appl. Phys. Lett.*, vol. 59, No. 2, Jul. 8, 1991, pp. 143–145.

Resolution Control of Low–Coherence Optical Time–Domain Reflectometer Between 14 and 290 $\mu$m by K. Takada, A. Himeno and K–i Yukimatsu, *IEEE Phot. Tech Lett.*, vol. 3, No. 7, Jul. 1991, pp. 676–678.

Phase–noise and shot–noise limited operations of low coherence optical time domain reflectometry by K. Takada, A. Himeno and K. Yukimatsu, *A. Phys. Lett.*, vol. 59, No. 20, Nov. 11, 1991, pp. 2483–2485.

Optical Coherence Tomography by Huang et al., *Science*, 254, Nov. 22, 1991, pp. 1178–1181.

Measurement of Corneal Thickness by Laser Doppler Interferometry by C.K. Hitzenberger, W. Drexler, and A.F. Fercher, *Inv. Ophth & Visual Sci.*, vol. 33, No. 1, Jan. 1992, pp. 98–103.

High–resolution reflectometry in biological tissues by X. Clivaz, F. Marquis–Weible, R.P. Salathe, R.P. Novak and H.H. Gilgen, *Optics Letters*, vol. 17, No. 1, Jan. 1, 1992, pp. 4–6.

Simultaneous Thickness and Group Index Measurement Using Optical Low–Coherence Reflectometry by W.V. Sorin and D.F. Gray, *IEEE Photonics Technology Letters*, vol. 4, No. 1, Jan. 1992, pp. 105–107.

High–speed optical coherence domain reflectometry by E.A. Swanson, D. Huang, M.R. Hee, J.G. Fujimoto, C.P. Lin, and C.A. Puliafito, *Optics Letters*, vol. 17, No. 2, Jan. 15, 1992, pp. 151–153.

Measurement of corneal thickness by low–coherence interferometry by C.K. Hitzenberger, *Applied Optics*, vol. 31, No. 31, Nov. 1, 1992, pp. 6637–6642.

In vivo retinal imaging by optical coherence tomography by E.A. Swanson, J.A. Izatt, M.R. Hee, D. Huang C.P. Lin, J.S. Schuman, and C.A. Puliafito, *Optics Letters*, vol. 18, No. 21, Nov. 1, 1993, pp. 1864–1866.

A Hardware–Compressive Fiber–Optic True Time Delay Steering System for Phased–Array Antennas by A. Goutzoulis, K, Davis, J. Zomp, P. Hrycak and A. Johnson, *Microwave J.*, Sep. 1994, pp. 126–140.

Photonic Aspects of Modern Radar, edited by H. Zmuda and E.N. Toughlican, *Artech House*, 1994, chapt 13: Switched Fiber–Optic Delay Architectures by A.P. Goutzoulis and D.K. Davies, pp. 351–380.

Coherent optical tomography of microscopic inhomogeneities in biological tissues by V.M. Gelikonov, G.V. Gelikonov, R.V. Kuranov, K.I. Pravdenko, A.M. Sergeev, F.I. Fel'dshtein, Ya.I. Khanin, D.V. Shabanov, N.D. Gladkova, N.K. Nikulin, G.A. Petrova and V.V. Pochinko, *JETP Lett.*, vol. 61, No. 2, Jan. 25, 1995, pp. 158–162.

Optical Coherence Tomography of the Human Retina by M.R. Hee, J.A. Izatt, E.A. Swanson, D. Huang, J.S. Schuman, C.P. Lin, C.A. Puliafito and J.G. Fujimoto, *Arch. Ophth.*, vol. 113, Mar. 1995, pp. 325–332.

Photonic Wideband Array Antennas by J.J. Lee, R.Y. Loo, S. Livingston, V.I. Jones, J.B. Lewis, H–W. Yen, G.L. Tangonan and M. Wechsberg, *IEEE Trans. Ant. and Propag*, vol. 43, No. 9, Sep. 1995, pp. 966–982.

In Vivo Endoscopic Optical Biopsy with Optical Coherence Tomography by G.J. Tearney, M.E. Brezinski, B.E. Bouma, S.A. Boppart, C. Pitris, J.F. Southern, and J.G. Fujimoto, *Science*, vol. 276, Jun. 27, 1997, pp. 2037–2039.

Array Transmitters and Their Application in RF–Photonics Systems by W. Ng, S. Bourgholtzer, D. Persechini, H.P. Hsu, H.W. Yen, G. Tangonan, A. Negri, P. Haugsjaa and M. Tabasky, *SPIE*, vol. 2844, pp. 146–152.

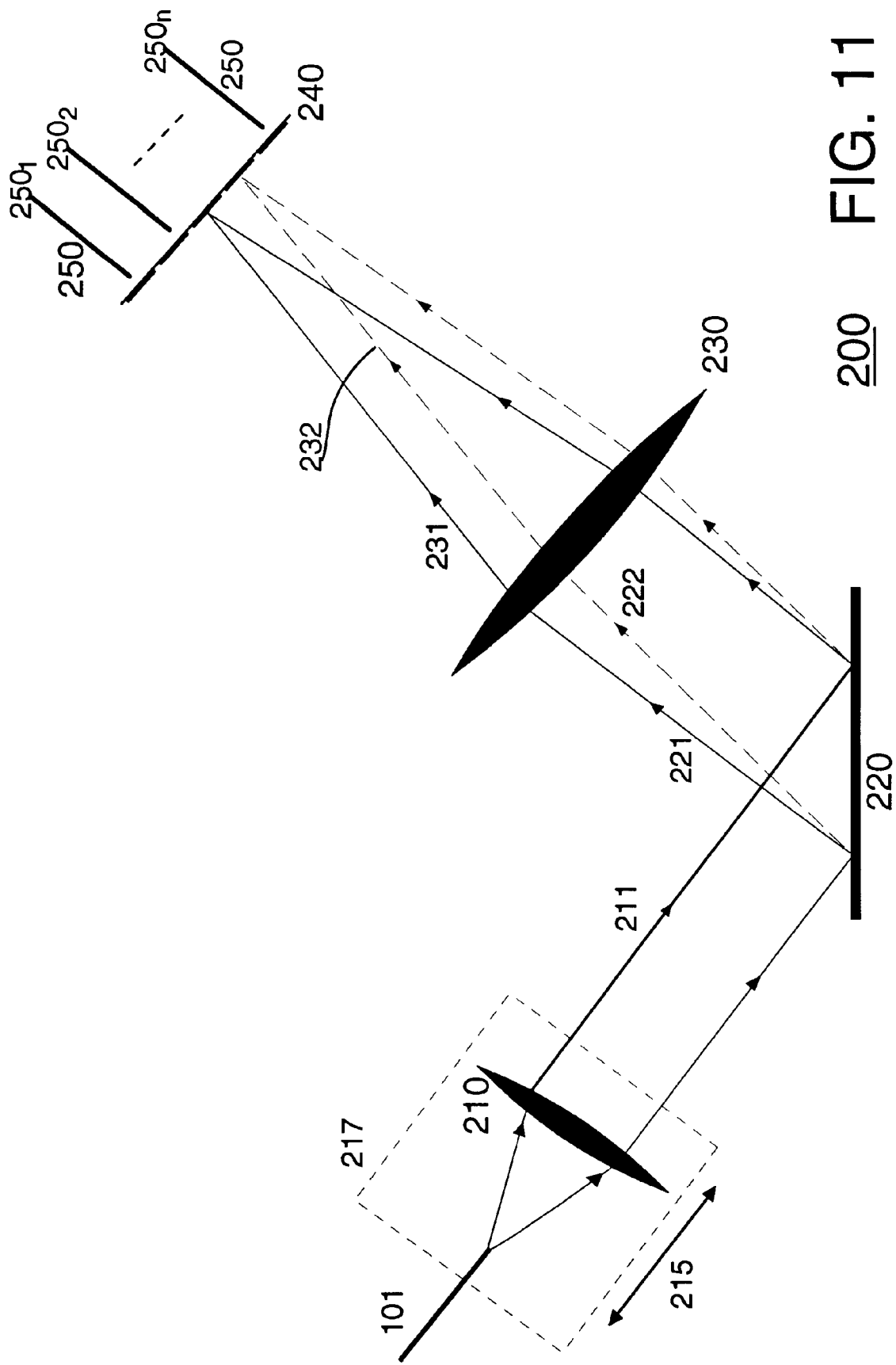

100

400

HIGH SPEED INSPECTION OF A SAMPLE USING COHERENCE PROCESSING OF SCATTERED SUPERBROAD RADIATION

TECHNICAL FIELD OF THE INVENTION

The present invention relates to inspection methods and inspection apparatus and, in particular, to high speed, high precision inspection methods and inspection apparatus using parallel processing.

BACKGROUND OF THE INVENTION

Optical coherence tomography ("OCT") apparatus are well known in the prior art. Such OCT apparatus can measure with micrometer resolution, and a typical example of such a prior art OCT apparatus includes a low coherence light source and a modified Michelson interferometer. Various embodiments of such prior art OCT apparatus have been developed for use in analyzing optical fibers and for use in medical applications to investigate biological tissue such as, for example, tissue in a human eye.

A typical OCT apparatus fabricated in accordance with the prior art splits radiation output from the low coherence light source into a reference beam and a probe beam. The reference beam is typically directed to a reference path which includes a device that varies the optical pathlength of the reference beam, the device typically being a moving reflector. The probe beam, on the other hand, is typically directed to a sample path which causes the probe beam to impinge upon a sample to be investigated. Radiation backscattered from various scattering centers in the sample is collected in the sample path. Next, the backscattered radiation output from the sample path is combined with radiation from the reference beam that is output from the reference path. The combined radiation is directed to impinge upon a detector.

Due to the low coherence of the radiation output from the low coherence light source of the typical prior art OCT apparatus, the detector only yields signals of interest whenever the optical pathlengths of the reference radiation output from the reference path and the backscattered radiation output from the sample path are substantially the same; within the coherence length of the radiation output from the low coherence light source.

The above-described prior art OCT apparatus has been used in medical applications with the objective of providing three dimensional ("3D") images of in vivo biological tissues with micrometer precision. However, problems arise with the use of the prior art OCT apparatus in such medical applications. The most important problem arises as a result of the relatively slow movement of a movable mirror that has typically been used to vary the optical pathlength of the reference path; the problem relates to uncontrollable motion of human tissue and to system noise. This problem makes it difficult, if not impossible, to achieve the objective of providing three dimensional images of in vivo biological tissues, especially when that objective includes mapping dynamic biological tissue such as that found in the human eye. For example, an article entitled "Optical Coherence Tomography of the Human Retina" by M. R. Hee, J. A. Izatt, E. A. Swanson, D. Huang, J. S. Schuman, C. P. Lin, C. A. Puliafito, and J. G. Fujimoto, in *Arch. Ophthalmol.*, Vol. 113, March 1995, pp. 325–329 discloses that "The 200 (horizontal)×250 (vertical) pixel image was acquired in 5 seconds and corresponds to a 5.6-mm cross section along the papillomacular axis of the retina." Thus, it would require over 16 minutes to use the disclosed OCT apparatus to provide a three dimensional map of the desired object, for example, a 200×200×250 pixel image. It should be readily apparent that this is impractical because it is almost impossible for a human subject to hold his/her eye motionless for such a long time. As a result, prior art OCT apparatus that only use a movable mirror to vary the optical pathlength of a reference path cannot solve the above-identified problem of providing 3D images of in vivo biological tissues.

One suggestion in the prior art for an alternative to using a moving reflector is to modulate radiation emitted by the low coherence light source with a linear frequency modulation (FM) chirp. Although this suggestion would remove the need for a movable reflector, it creates still other problems. For example, in order for the OCT apparatus to provide micrometer resolution, the FM chirp needs to be more than ten percent (10%) of the central source frequency. However, such a wideband FM chirp cannot be provided with present technology.

A further problem that occurs with the prior art OCT apparatus occurs as a result of the fact that the resolution depends on the bandwidth of the radiation output by the low coherence light source. For examining biological tissue, a preferred light source should output radiation that is not absorbed by common constituents of biological tissue such as, for example, water and melanin. This is to enable the radiation to penetrate deeply into the sample tissue and to enable the OCT apparatus to provide images of tissues having a small backscattering cross section. The further problem is that only certain light sources output radiation in suitable frequency bands. Additionally, a still further problem occurs in that, even if the low coherent light source outputs radiation in the desired frequency band, the output radiation may not have enough power to enable the OCT apparatus to take advantage of the ability of the output radiation to penetrate deeply into the sample.

In light of the above, there is a need in the art for a high speed, high precision inspection method and apparatus that overcomes the above-identified problems.

SUMMARY OF THE INVENTION

Advantageously, embodiments of the present invention are method and apparatus that solve the above-identified problems in the art and provide high speed, high precision inspection methods and apparatus.

In particular, an embodiment of a first aspect of the present invention is an inspection apparatus for inspecting a sample that uses parallel processing and which comprises: (a) a source of radiation which outputs superbroad inspection radiation having a frequency spectrum with an inspection width and one or more reference radiation outputs, each of the one or more reference radiation outputs having a reference frequency spectrum with a reference width that is less than or substantially equal to the inspection width; (b) an inspection applicator apparatus which applies the inspection radiation as input to the sample; (c) an inspection collection apparatus which applies at least a portion of the inspection radiation that is scattered by the sample as input to a dispersal apparatus; (d) a reference collection apparatus which applies radiation from the one or more reference radiation outputs as input to the dispersal apparatus; (e) wherein the dispersal apparatus applies radiation from the scattered inspection radiation as input to a plurality of coherence processors and applies radiation from the one or more reference radiation outputs to the plurality of coherence processors; (f) wherein the width of the frequency spectrum of the radiation from the scattered inspection radiation that is applied as input to the coherence processors and the width of the frequency spectrum of the radiation from the one or more reference radiation outputs that is applied as input to the coherence processors satisfy at least one of the following: (i) the width of the frequency spectrum of the radiation from the scattered inspection radiation is substantially the same as the inspection width and the width of the frequency spectrum of the radiation from the one or more reference radiation outputs is less than the inspection width; or (ii) the width of the frequency spectrum of the radiation from the scattered inspection radiation is less than the inspection width and the width of the frequency spectrum of the radiation from the one or more reference radiation outputs is substantially the same as the inspection width; or (iii) the width of the frequency spectrum of the radiation from the scattered inspection radiation is less than the inspection width and the width of the frequency spectrum of the radiation from the one or more reference radiation outputs is less than the inspection width.

An embodiment of a second aspect of the present invention is an inspection apparatus for inspecting a sample that uses parallel processing and which comprises: (a) a source of radiation which outputs superbroad inspection radiation and superbroad reference radiation; (b) an inspection applicator apparatus which applies the inspection radiation as input to the sample; (c) an inspection collection apparatus which applies at least a portion of the inspection radiation that is scattered by the sample as input to a dispersal apparatus; (d) a reference collection and delay apparatus produces a predetermined number of reference radiation outputs having predetermined delays with respect to one another and applies the reference radiation outputs as inputs to the dispersal apparatus; and (e) wherein the dispersal apparatus applies radiation from the scattered inspection radiation as input to a coherence processor and applies radiation from the reference radiation outputs as input to the coherence processor.

An embodiment of a third aspect of the present invention is an inspection apparatus for inspection of wafers, masks such as photomasks, and the like used in the semiconductor industry to fabricate circuits, memory, and the like and which comprises: (a) a source of radiation which outputs superbroad inspection radiation and superbroad reference radiation; (b) a radiation applicator apparatus which applies the inspection radiation as input to the sample and which applies the reference radiation as input to a reference; and (c) a radiation collection apparatus which applies at least a portion of the inspection radiation scattered by the sample as input to a defect processor and which applies at least a portion of the reference radiation scattered by the sample as input to the defect processor.

BRIEF DESCRIPTION OF THE FIGURE

A complete understanding of the present invention may be gained by considering the following detailed description in connection with the accompanying drawings in which:

FIG. 11 shows, in pictorial form, a spectrum separator that is used to fabricate embodiments of the present invention;

FIG. 24–26 show block diagrams of inspection apparatus that are fabricated in accordance with the third aspect of the present invention for use, for example, in inspecting wafers, photomasks, and the like used in the semiconductor industry to fabricate circuits, memory, and the like.

Components which are the same in the various figures have been designated by the same numerals for ease of understanding.

DETAILED DESCRIPTION

The following is a description of an embodiment of a first aspect of the present invention, which description provides a broad overview of the first aspect of the present invention.

Figure 1:
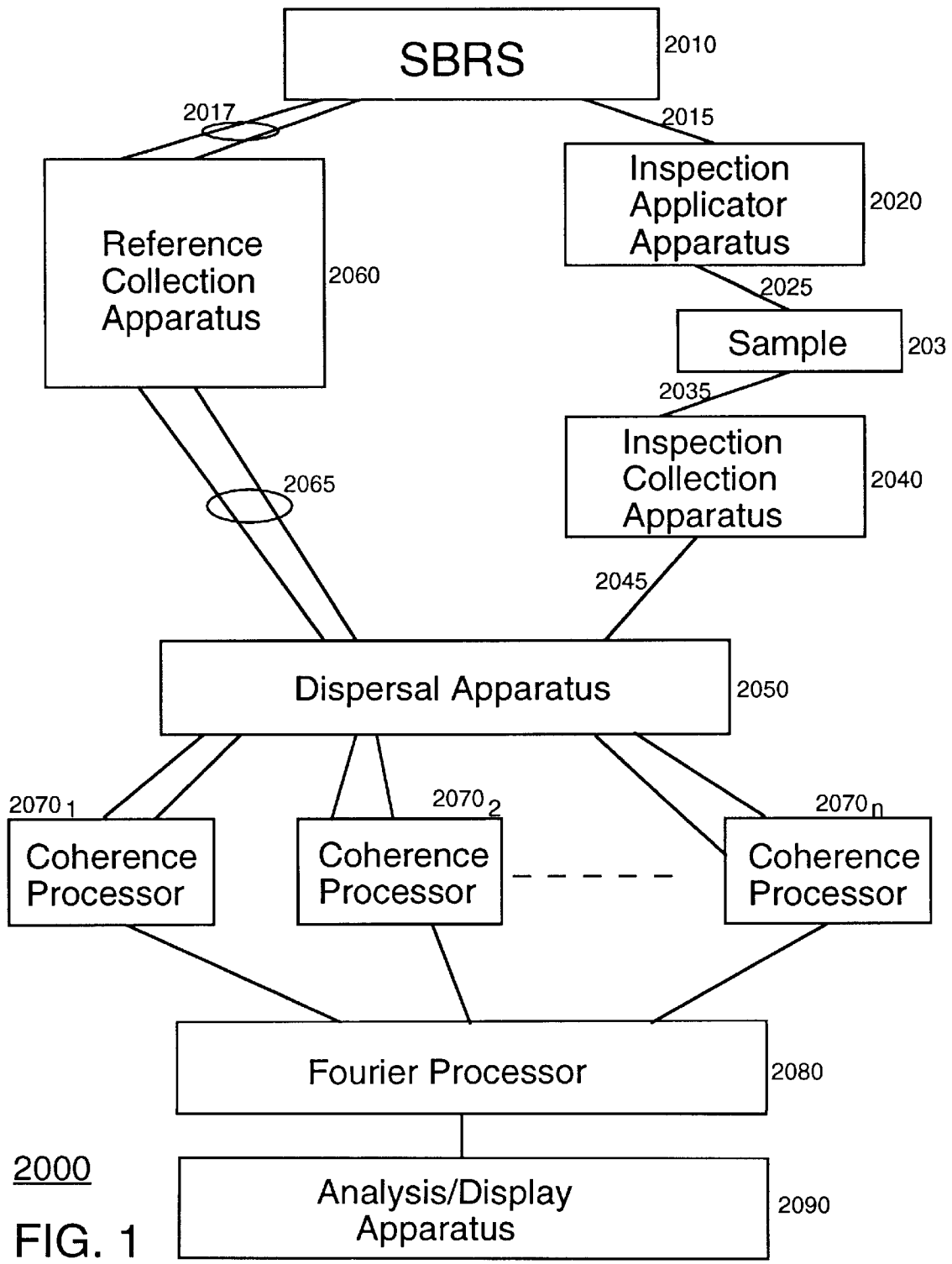
FIG. 1 shows a block diagram of an inspection apparatus that is fabricated in accordance a first aspect of the present invention.

FIG. 1 shows a block diagram of inspection apparatus 2000 that is fabricated in accordance with the first aspect of the present invention. As shown in FIG. 1, inspection apparatus 2000 includes superbroad radiation source 2010 ("SBRS 2010") which outputs superbroad inspection radiation 2015 having a frequency spectrum with a frequency width that will referred to below as an inspection width. The term superbroad radiation will be described in detail below. SBRS 2010 outputs superbroad inspection radiation 2015 and applies it as input to inspection applicator apparatus 2020, and inspection applicator apparatus 2020, in turn, applies inspection radiation 2025 as input to sample 2030. Next, inspection collection apparatus 2040 collects at least a portion of the inspection radiation that is scattered by sample 2030 (scattered inspection radiation 2035), and inspection collection apparatus 2040, in turn, applies scattered inspection radiation 2045 as input to dispersal apparatus 2050.

As is also shown in FIG. 1, SBRS 2010 outputs reference radiation as one or more reference radiation outputs 2017, each of which one or more reference radiation outputs 2017 has a frequency spectrum with a frequency width that will be referred to below as a reference width (the reference width is less than or substantially equal to the inspection width). SBRS 2010 outputs the one or more reference radiation outputs 2017 and applies it or them as input to reference collection apparatus 2060, and reference collection apparatus 2060, in turn, applies one or more reference radiation outputs 2065 as input to dispersal apparatus 2050.

Next, dispersal apparatus 2050 applies radiation from scattered inspection radiation 2045 as input to a plurality of coherence processors $2070_1, 2070_2, \ldots, 2070_n$ and applies radiation from one or more of reference radiation outputs 2065 as input to the plurality of coherence processors $2070_1, 2070_2, \ldots, 2070_n$. Next, outputs from coherence processors $2070_1, 2070_2, \ldots, 2070_n$ are applied as input to Fourier processor 2080. Finally, output from Fourier processor 2080 is applied as input to analysis/display apparatus 2090. Embodiments of SBRS 2010, inspection applicator apparatus 2020, inspection collection apparatus 2040, reference collection apparatus 2060, dispersal apparatus 2050, coherence processors $2070_1, 2070_2, \ldots, 2070_n$, Fourier processor 2080, and analysis/display apparatus 2090 will be described in detail below.

In accordance with the present invention, the width of the frequency spectrum of the radiation from the scattered inspection radiation that is applied as input to coherence processors $2070_1, 2070_2, \ldots, 2070_n$ and the width of the frequency spectrum of the radiation from the one or more reference radiation outputs that is applied as input to coherence processors $2070_1, 2070_2, \ldots, 2070_n$ satisfy one of the following requirements.

Requirement 1: the width of the frequency spectrum of the radiation from the scattered inspection radiation is substantially the same as the inspection width and the width of the frequency spectrum of the radiation from the one or more reference radiation outputs is less than the inspection width.

Requirement 2: the width of the frequency spectrum of the radiation from the scattered inspection radiation is less than the inspection width and the width of the frequency spectrum of the radiation from the one or more reference radiation outputs is substantially the same as the inspection width.

Requirement 3: the width of the frequency spectrum of the radiation from the scattered inspection radiation is less than the inspection width and the width of the frequency spectrum of the radiation from the one or more reference radiation outputs is less than the inspection width.

The following describes embodiments of superbroad radiation sources used to fabricate embodiments of the present invention.

As used herein, the term superbroad radiation refers to radiation having a frequency spectrum with a "broad frequency width." The term broad frequency width means a frequency width which is sufficiently broad that it can provide a pulse that produces small spatial gating, i.e., spatial gating of less than or on the order of 30 $\mu$m. Spatial gating is defined as the distance traversed by radiation in a time corresponding to the temporal pulse width. For example, a 25 femtosecond pulse ($25 \times 10^{-15}$ sec or 25 fs) produces a 7.5 $\mu$m spatial gating, i.e., the spatial gating equals the speed of light multiplied by the pulse width. Further, the frequency width is nearly given by 1/(pulse width).

One embodiment of a superbroad radiation source is a source of low coherence radiation. A source of low coherence radiation may be a light emitting diode, a superluminescent diode, or any other source of low coherent radiation (including those which are known to, or can be designed by, those skilled in the art). Thus, whenever the term low coherence radiation source is used herein, it is meant to be used in its most general and inclusive sense.

Figure 4:
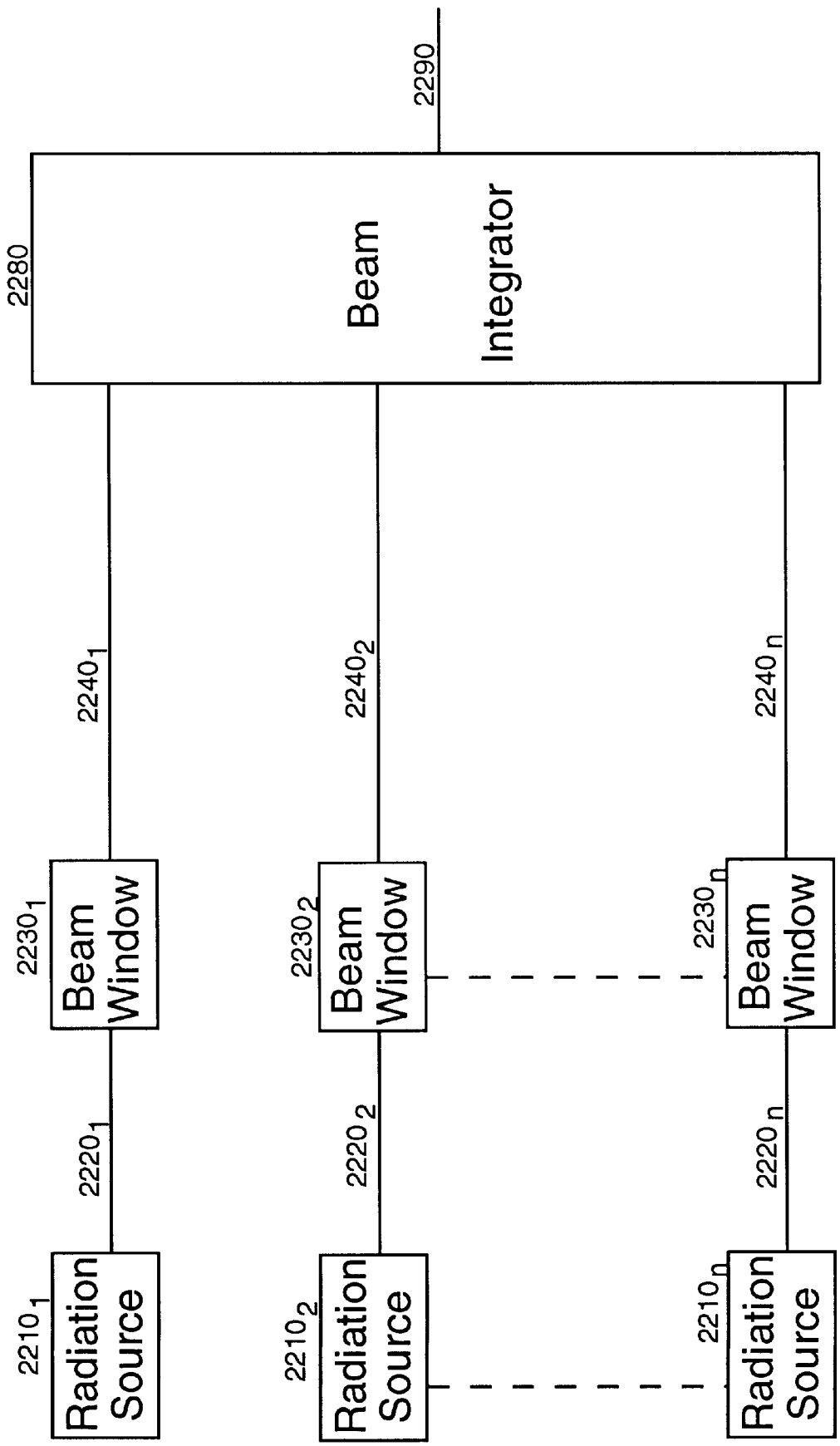
FIG. 4 shows a block diagram of a source of superbroad radiation that includes a multiplicity of radiation sources, which source of superbroad radiation is used to fabricate embodiments of the present invention.

Another superbroad radiation source is provided in accordance with the embodiment of superbroad radiation source 2200 shown in FIG. 4. As shown in FIG. 4, SBRS 2200 includes a multiplicity of radiation sources $2210_1, 2210_2, \ldots, 2210_n$ which output radiation and apply the radiation as input to optical paths $2220_1, 2220_2, \ldots, 2220_n$, respectively. The outputs from optical paths $2220_1, 2220_2, \ldots, 2220_n$ are applied as input to beam windows $2230_1, 2230_2, \ldots, 2230_n$, respectively. In the following, an optical path can be fabricated using bulk optical components such as lens systems, reflectors, prisms and so forth, optical fibers, optical waveguides, integrated optical components, and any combinations of the foregoing (including any which are known to, or can be designed by, those skilled in the art). In addition, whenever the term optical path is used, the term also contemplates embodiments wherein radiation is applied directly from one device, component, or apparatus to another. Thus, whenever the term optical path is used herein, it is meant to be used in its most general and inclusive sense.

Each of beam windows $2230_1, 2230_2, \ldots, 2230_n$ is a device for adjusting pulse width, and hence the frequency spectrum, of radiation output from radiation sources $2210_1, 2210_2, \ldots, 2210_n$, respectively, to predetermined widths. As is well known to those of ordinary skill in the art, such beam windows may be fabricated in a number of ways such as by the use of pulse compression techniques, beam chopping techniques, prisms, gratings, filters, and so forth (including any which are known to, or can be designed by, those skilled in the art). Thus, whenever the term beam window is used herein, it is meant to be used in its most general and inclusive sense.

The radiation outputs from beam windows $2230_1, 2230_2, \ldots, 2230_n$ are applied as input to optical paths $2240_1, 2240_2, \ldots, 2240_n$, respectively, and the outputs from optical paths $2240_1, 2240_2, \ldots, 2240_n$ are applied, in turn, as inputs to beam integrator 2280. Beam integrator 2280 is apparatus which combines the radiation applied as inputs from optical paths $2240_1, 2240_2, \ldots, 2240_n$ into a single beam of radiation and applies the single beam of radiation, in turn, as input to optical path 2290. Embodiments of beam integrator 2280 will be described in detail below in connection with FIG. 7.

In accordance with the present invention, superbroad radiation can be formed, for example, using a superluminescent diode having a pulse width of 25 fs (frequency width $\Delta f = 4 \times 10^{13}$ Hz) and a frequency spectrum having a central frequency $f = 3 \times 10^{14}$ Hz (this just serves as an example for ease of understanding the present invention). Alternatively, superbroad radiation can be formed using the embodiment of FIG. 4 with, just to serve as an example for ease of understanding the present invention, 100 independent lasers, each laser having the same pulse width of 2.5 ps (frequency width $\Delta f_{las} = 4 \times 10^{11}$ Hz), wherein the 100 lasers have frequency spectra with, just to serve as an example for ease of understanding the present invention, central frequencies of $f \pm n \Delta f_{las}$ where $n=1, 2, \ldots, 50$. As a further alternative, if one were to use 200 short pulse lasers, each having the same pulse width of 2.5 ps, and the 200 lasers have frequency spectra with central frequencies of $f \pm n \Delta f_{las}$ where $n=1, 2, \ldots, 100$, then the superbroad radiation output from the embodiment shown in FIG. 4 would be equivalent to that produced, for example, by a superluminescent diode having a 12.5 fs pulse width. If one or more of the radiation sources (for example, lasers) used to fabricate a superbroad radiation source in accordance with the embodiment of FIG. 4 were to have a pulse width that is shorter than, for example, 2.5 ps, the pulse width can be stretched, for example, by using a spectrum separator (to be described in detail below) to reduce the width of the frequency spectrum. If, on the other hand, one or more of the radiation sources (for example, lasers) used to fabricate a superbroad radiation source in accordance with the embodiment of FIG. 4 were to have a pulse width that is longer than, for example, 2.5 ps, then, as was described above, a beam widow can be used to reduce the pulse width. Thus, the term beam window is used in its most general sense as a device to produce radiation having a frequency spectrum with a predetermined frequency width. Therefore, in some cases the beam window shortens a pulse, in other cases the beam window lengthens a pulse, and in still other cases, it merely transmits a pulse. It should be noted that the present invention does not require the pulse width of each beam of radiation input to beam integrator 2280 be the same in order to provide superbroad radiation.

Figure 5:
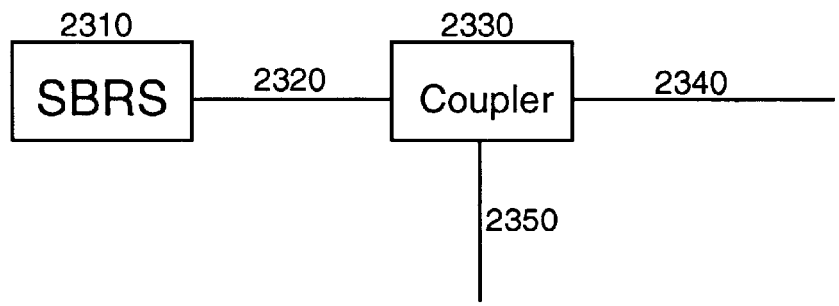
FIGS. 5 and 6 show further sources of superbroad radiation that are used to fabricate embodiments of the present invention.
Figure 6:
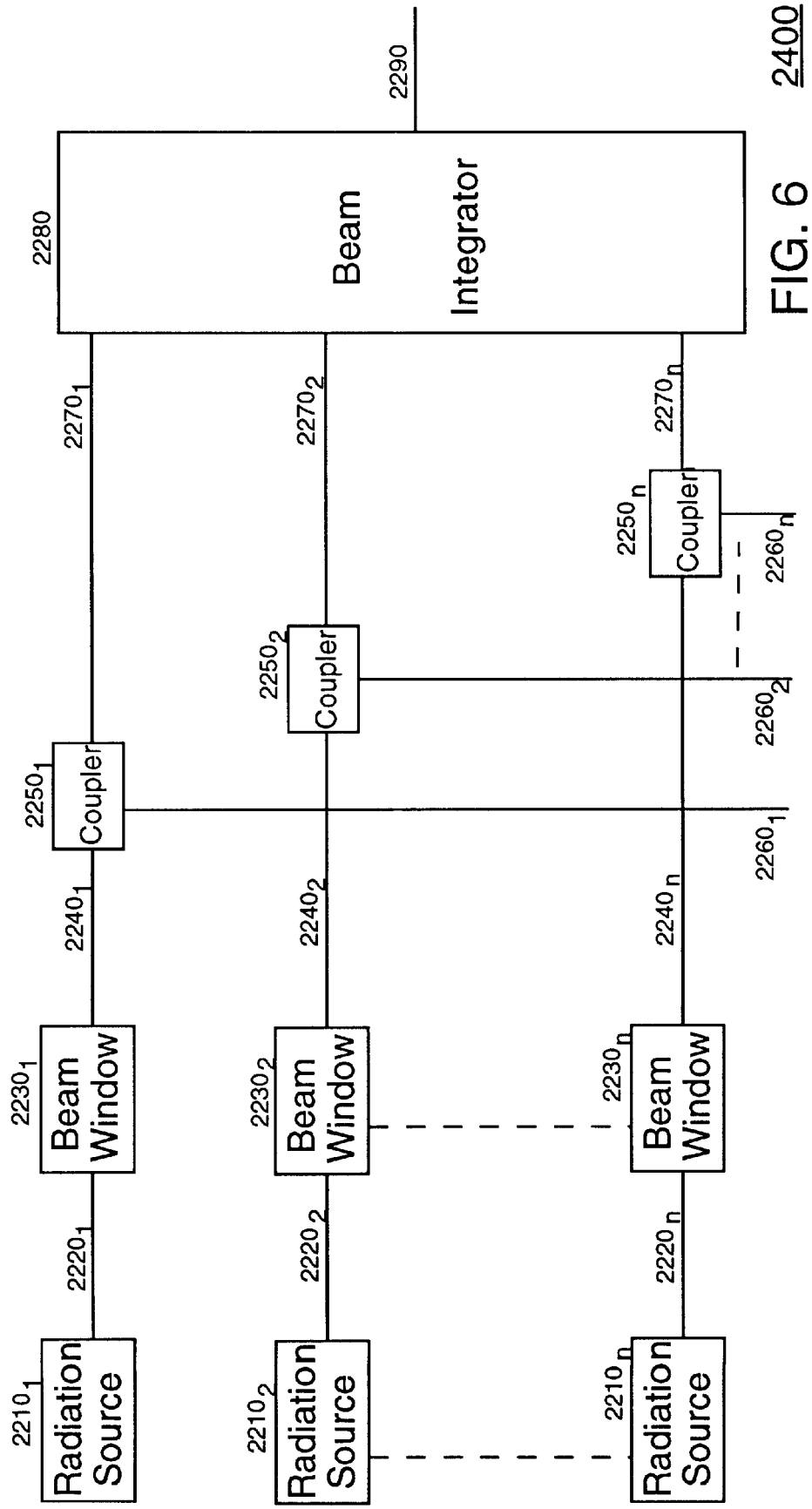

FIGS. 5 and 6 show further embodiments of superbroad radiation sources. As shown in FIG. 5, SBRS 2310 outputs superbroad radiation and applies it as input to optical path 2320. The output from optical path 2310 is applied as input to coupler 2330. Coupler 2330 applies a first portion of the input superbroad radiation as input to optical path 2340 and applies a second portion of the input superbroad radiation as input to optical path 2350. Coupler 2330 may be fabricated in many ways, including any which are known to, or can be designed by, those skilled in the art. For example, coupler 2330 can be embodied to provide the desired finction in bulk optics, in optical fibers, in integrated optics, and so forth as well as any combination of the foregoing. Specifically, coupler 2330 may be an optical fiber coupler wherein the radiation travels in optical fibers and coupler 2330 may be comprised of beamsplitter apparatus, as well as combinations of such apparatus. Thus, whenever the term coupler is used herein, it is meant to be used in its most general and inclusive sense.

As shown in FIG. 6, SBRS 2400 includes a multiplicity of radiation sources $2210_1, 2210_2, \ldots, 2210_n$ which output radiation and apply the radiation as input to optical paths $2220_1, 2220_2, \ldots, 2220_n$, respectively. The outputs from optical paths $2220_1, 2220_2, \ldots, 2220_n$ are applied as input to beam windows $2230_1, 2230_2, \ldots, 2230_n$, respectively. Next the radiation outputs from beam windows $2230_1, 2230_2, \ldots, 2230_n$ are applied as inputs to optical paths $2240_1, 2240_2, \ldots, 2240_n$, respectively, and the outputs from optical paths $2240_1, 2240_2, \ldots, 2240_n$ are applied, in turn, as inputs to couplers $2250_1, 2250_2, \ldots, 2250_n$, respectively. Next, couplers $2250_1, 2250_2, \ldots, 2250_n$ apply a first portion of the input radiation as input to optical paths $2260_1, 2260_2, \ldots, 2260_n$, respectively, and apply a second portion of the input radiation as input to optical paths $2270_1, 2270_2, \ldots, 2270_n$, respectively. Radiation outputs from optical paths $2270_1, 2270_2, \ldots, 2270_n$ are applied as inputs to beam integrator 2280. Beam integrator 2280 combines the radiation applied as inputs from optical paths $2270_1, 2270_2, \ldots, 2270_n$ into a single beam of radiation and applies the single beam of radiation, in turn, as input to optical path 2290.

Figure 7:
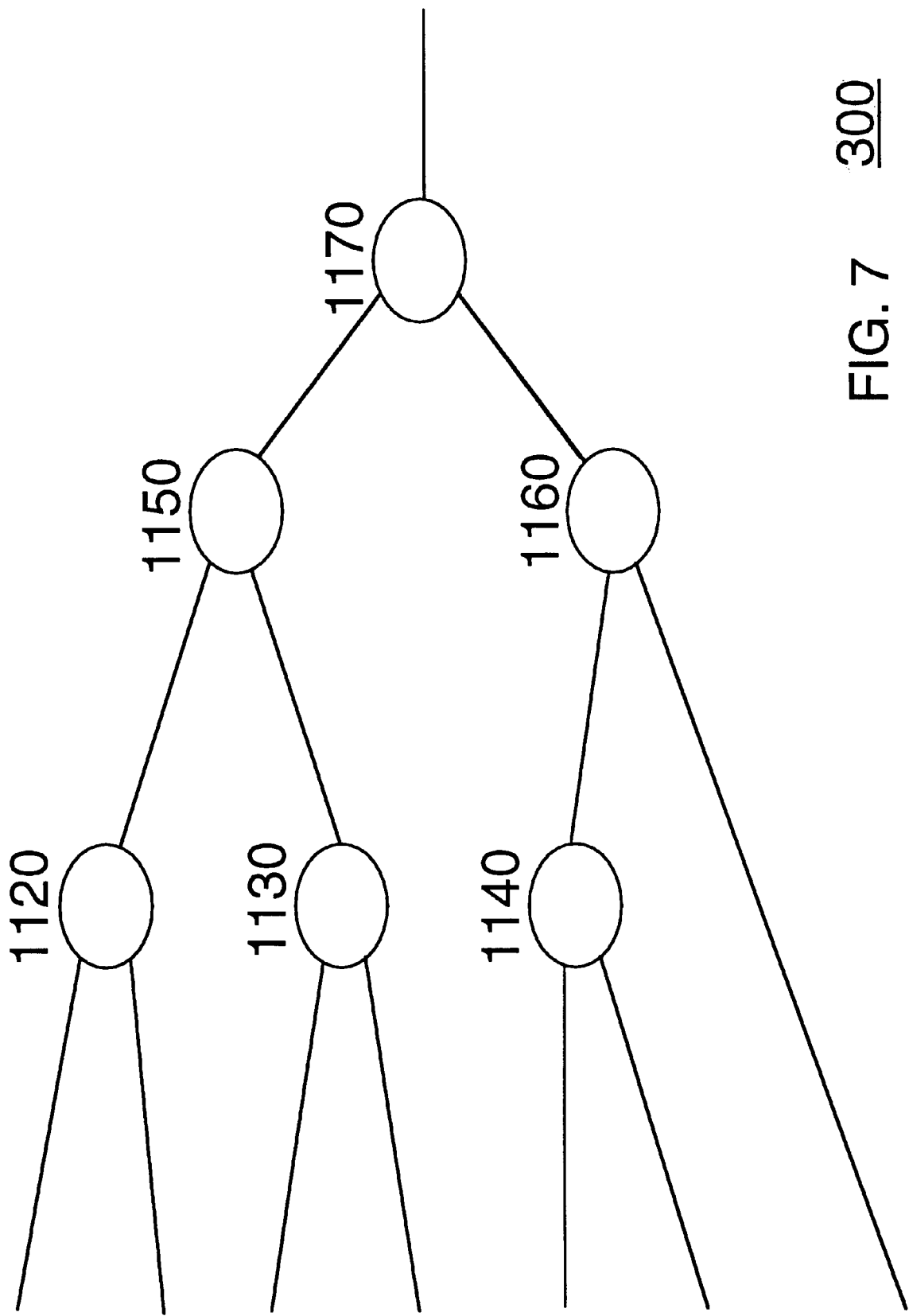
FIG. 7 shows, in pictorial form, a beam integrator that is used to fabricate embodiments of the present invention.

FIG. 7 shows, in pictorial form, beam integrator 300 which combines multiple input beams into a single output beam for use in fabricating embodiments of the present invention. As shown in FIG. 7, beam integrator 300 comprises couplers 1120, 1130, 1140, 1150, 1160, and 1170, each of which couplers combines two input optical paths into one output optical path. As those of ordinary in the art should readily appreciate, many different and varied embodiments of beam integrators can be used to fabricate embodiments of the present invention and, as such, beam integrator 300 shown in FIG. 7 is shown for illustration purposes only. It is noted that the term optical path, as was mentioned above, is used in its most general sense. A preferred beam integrator should have low loss. As those of ordinary skill in the art can readily appreciate, in designing an inspection apparatus in accordance with the present invention, it is important to take into account the optical pathlength of each optical path as well as optical pathlength differences that occur between different inputs. Thus, a preferred beam integrator will minimize optical pathlength delays introduced by optical paths, optical couplers, and the like within beam integrator 300. Further, the preferred beam integrator will minimize these optical pathlength delays, and will not introduce optical pathlength differences among different optical paths. As those of ordinary skill in the art should further appreciate, these optical paths, optical couplers, and the like may be integrated to form a chip to reduce the size and cost of beam integrator 300.

Figure 2:
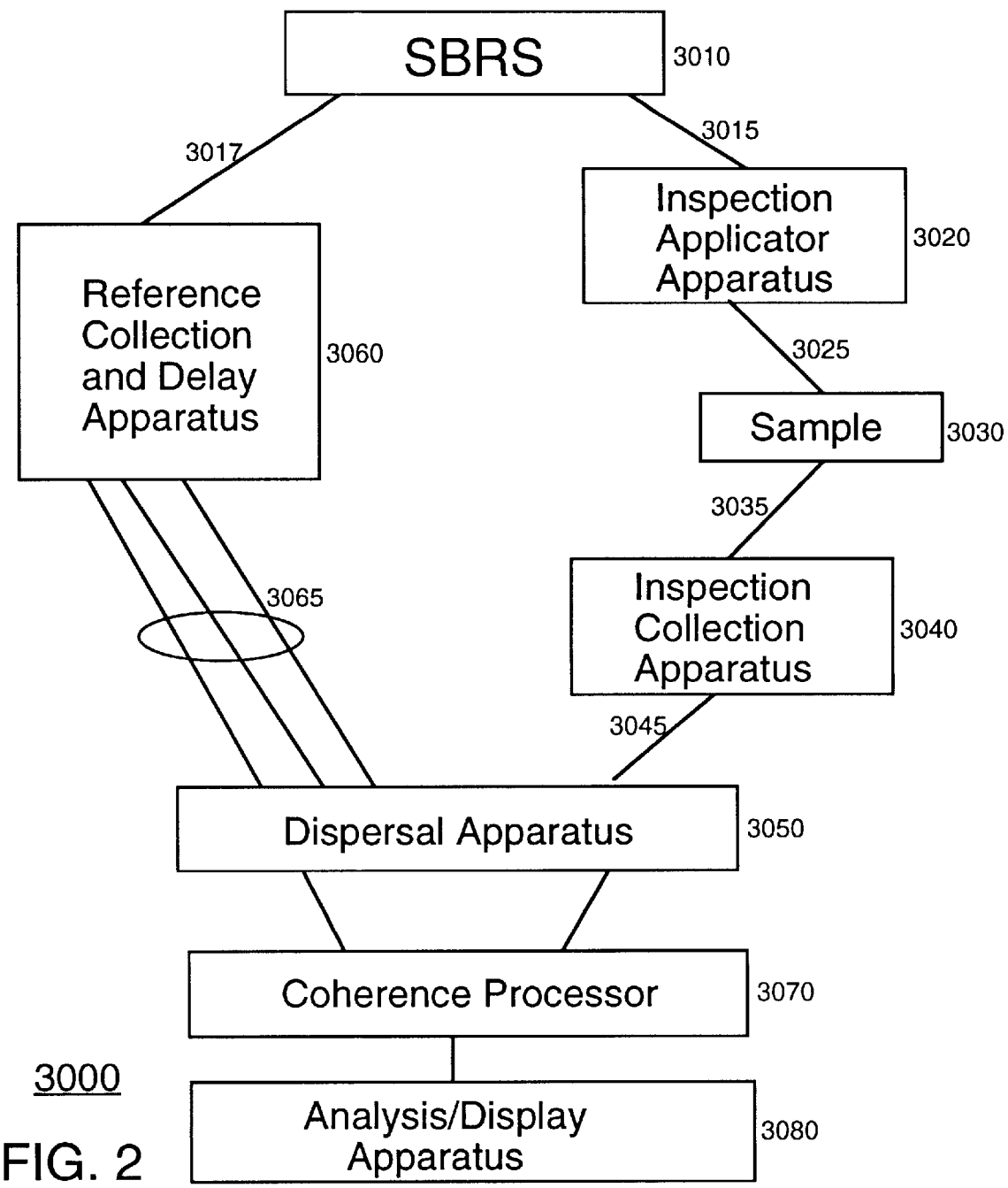
FIG. 2 shows a block diagram of an inspection apparatus that is fabricated in accordance with a second aspect of the present invention.
Figure 8:
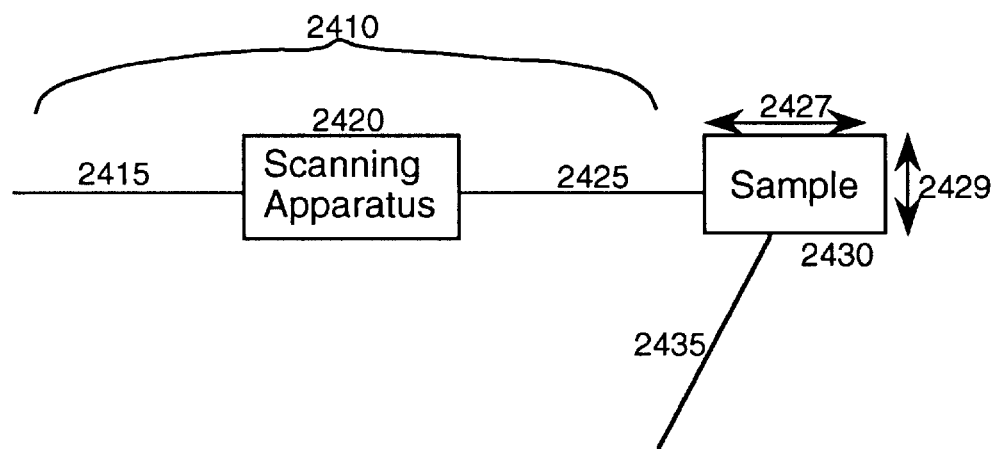
FIGS. 8–9 show block diagrams of an inspection applicator apparatus and an inspection collection apparatus that are used to fabricate embodiments of the present invention.

FIG. 8 shows, in pictorial form, an inspection applicator apparatus and an inspection collection apparatus for use in fabricating embodiments of the present invention such as, for example, embodiments shown in FIGS. 1 and 2. As shown in FIG. 8, superbroad inspection radiation is applied as input to optical path 2415, and output from optical path 2415 is applied, in turn, as input to scanning apparatus 2420. Scanning apparatus 2420 scans the inspection radiation in a transverse direction across sample 2430 (for example a human eye) over optical path 2425. The term transverse direction means to scan the inspection radiation so that it examines portions of sample 2430 that lie in a plane perpendicular to a particular direction in which the inspection radiation is applied to a sample. For example, for the embodiment shown in FIG. 8, the transverse direction includes portions of sample 2430 that lie in a plane that are perpendicular to the specific direction that inspection radiation travels when output from optical path 2425 that is shown in FIG. 8. Thus, transverse direction is considered relative to a particular predetermined direction of radiation output from an optical path.

Scanning apparatus 2420 is fabricated in accordance with many methods and apparatus (including any which are known to, or can be designed by, those skilled in the art). For example, a number of suitable embodiments of scanning apparatus 2420 are found in U.S. Pat. No. 5,321,501 (the Swanson et al. patent), the specification of which patent is incorporated by reference herein. Thus, whenever the term scanning apparatus is used herein, it is meant to be used in its most general and inclusive sense.

Next, as shown in FIG. 8, inspection radiation that is scattered by sample 2430 is applied as input to optical path 2435. In an alternative of the embodiment shown in FIG. 8, scanning apparatus 2420 is omitted, or used in part, and some of the role, if not all of the role, played by scanning apparatus 2420 is provided by a sample moving apparatus (not shown) that moves sample 2430, for example, in one or more of three dimensions, including one or both of the directions indicated by arrows 2427 and 2429, respectively. The sample moving apparatus can be, for example, a movable table top on which sample 2430 is disposed. Thus, whenever the term sample moving apparatus is used herein, it is meant to be used in its most general and inclusive sense. As one can readily appreciate, the inspection radiation that is collected can be scattered in any direction, including the forward direction, if this is possible for the particular sample being inspected. For example, if the sample is an eye it may be difficult to collect radiation that is scattered in the forward direction.

Figure 9:
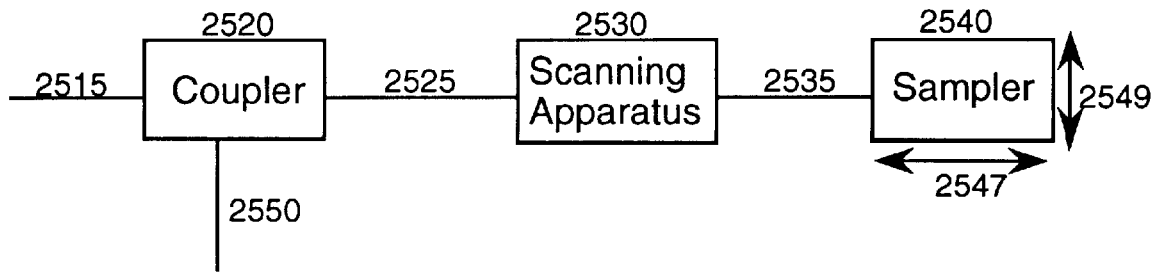

FIG. 9 shows, in pictorial form, an inspection applicator apparatus and an inspection collection apparatus for use in fabricating embodiments of the present invention such as, for example, embodiments shown in FIGS. 1 and 2 which collect radiation that is backscattered from a sample. As shown in FIG. 9, superbroad inspection radiation is applied as input to optical path 2515, and output from optical path 2415 is applied, in turn, as input to coupler 2520. Inspection radiation output from coupler 2520 is applied as input to optical path 2525 and output from optical path 2525 is applied, in turn, as input to scanning apparatus 2530. Scanning apparatus 2530 scans the inspection radiation in a transverse direction across sample 2540 (for example a human eye) over optical path 2535. Radiation that is backscattered from sample 2540 is applied as input to optical path 2535. Next, the backscattered inspection radiation output from optical path 2535 is applied as input to scanning apparatus 2530, and scanning apparatus 2530, in turn, applies the backscattered radiation as input to optical path 2525. Next, backscattered inspection radiation output from optical path 2525 is applied as input to coupler 2520, and coupler 2520, in turn, applies the backscattered inspection radiation as input to optical path 2550. In an alternative of the embodiment shown in FIG. 9, scanning apparatus 2530 is omitted, or used in part, and some of the role, if not all of the role, played by scanning apparatus 2530 is provided by a sample moving apparatus (not shown) that moves sample 2540, for example, in one or more of three dimensions, including one or both of the directions indicated by arrows 2547 and 2549, respectively.

Reference collection apparatus for use in fabricating embodiments of the present invention such as, for example, embodiments shown in FIG. 1 are comprised of one or more optical paths, depending on the number of reference radiation outputs from the superbroad radiation source. Further, the reference radiation output from the optical paths are applied as input to a dispersal apparatus.

Figure 10:
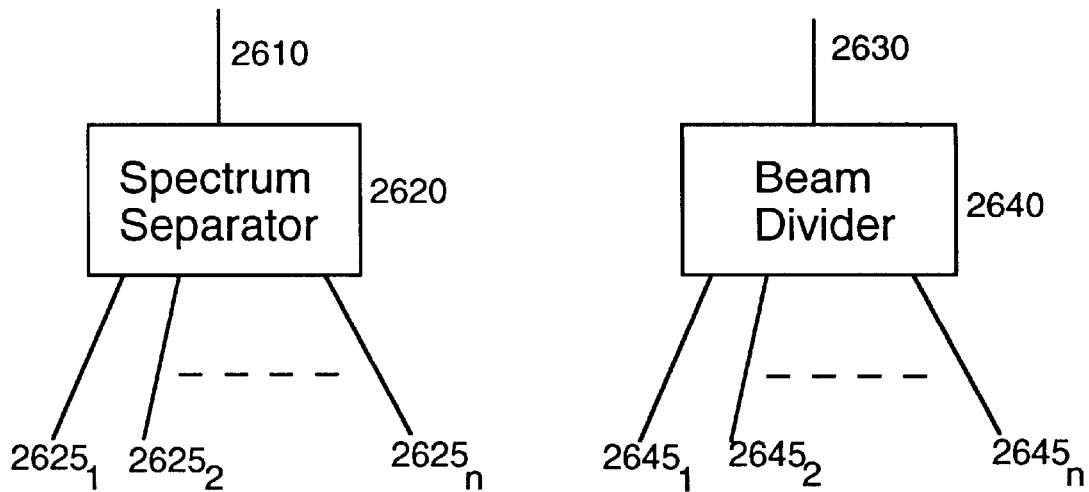
FIG. 10 shows a block diagram of a dispersal apparatus that is used to fabricate embodiments of the first aspect of the present invention.

FIG. 10 shows, in pictorial form, a dispersal apparatus for use in fabricating embodiments of the first aspect of the present invention, for example, embodiments shown in FIG. 1. As shown in FIG. 10, superbroad reference radiation output from optical path 2610 is applied as input to spectrum separator 2620 and scattered inspection radiation output from optical path 2630 is applied as input to beam divider 2640. Spectrum separator 2620 is an apparatus that divides the radiation applied as input from optical path 2610 into multiple beams in accordance with the contents of the frequency spectrum of the input radiation and applies the multiple beams, in turn, as inputs to optical paths $2625_1$, $2625_2$, ..., $2625_n$, respectively. Embodiments of spectrum separator 2620 will be described in detail below in connection with FIG. 11. The center frequency and width of the frequency spectrum of each of the multiple beams output from spectrum separator 2620, as will be described below in connection with FIG. 11, are determined by the center and width of its corresponding frequency spectrum window at spectrum separator 2620. As those of ordinary skill in the art should readily appreciate, the difference between the highest and lowest center frequencies of the frequency spectra of the multiple beams is limited by the width of the frequency spectrum of the radiation applied as input from optical path 2610.

Beam divider 2640 is an apparatus that divides the radiation applied as input from optical path 2630 into multiple beams and applies the multiple beams, in turn, as input to optical paths $2645_1$, $2645_2$, ..., $2645_n$, respectively. Embodiments of beam divider 2640 will be described in detail below in connection with FIG. 12. The useful number of multiple beams that beam divider 2640 can provide depends on the intensity of the superbroad radiation output from optical path 2630. The intensity of the scattered inspection radiation output from optical path 2630 is usually lower than the intensity of the reference radiation output from optical path 2610. If necessary, in a particular embodiment, this difference in intensity can be overcome, in principle, by appropriately amplifying the scattered inspection radiation by use of optical amplifiers in any one of a number of places, for example, in optical path 2630. Alternatively, one or more of the multiple beams applied as input to optical paths $2645_1$, $2645_2$, ..., $2645_n$ may be amplified also (or instead of amplification in, for example, optical path 2630). Further, as will become apparent from the further discussion below, one or more of the multiple beams that are applied as input to optical paths $2645_1$, $2645_2$, ..., $2645_n$ may advantageously be amplified in narrow frequency bands. It should also be noted that the technique of amplification in narrow frequency bands may also be applied to various portions of the frequency spectrum of the inspection radiation and/or to the scattered inspection radiation. Many ways of fabricating appropriate amplifiers are known to those of ordinary skill in the art. Thus, whenever the term amplifier is used herein, it is meant to be used in its most general and inclusive sense.

We now return to inspection apparatus 2000 shown in FIG. 1. In accordance with the embodiment shown in FIG. 1, the radiation output from optical paths $2625_1$, $2625_2$, ..., $2625_n$ and the radiation output from optical paths $2645_1$, $2645_2$, ..., $2645_n$ are applied, pairwise, to coherence processors $2070_1$, $2070_2$, ..., $2070_n$, respectively. Coherence processors $2070_1$, $2070_2$, ..., $2070_n$ measure coherent interference between radiation output from optical paths $2625_1$, $2625_2$, ..., $2625_n$ formed from the reference radiation and radiation output from optical paths $2645_1$, $2645_2$, ..., $2645_n$ formed from the scattered inspection radiation. Preferably, the coherence processors utilize optical heterodyne techniques that are known to those of ordinary skill in the art to measure coherent interference between radiation output from optical paths $2625_1$, $2625_2$, ..., $2625_n$ formed from the reference radiation and radiation output from optical paths $2645_1$, $2645_2$, ..., $2645_n$ formed from the scattered inspection radiation. However, as is known to those of ordinary skill in the art, the optical heterodyne techniques produce many non-coherent outputs along with the coherent interference outputs. As is further known to those of ordinary skill in the art, a known beat signal can be used to enhance detection of the coherent interference outputs in the presence of the non-coherent outputs. It is yet further known to those of ordinary skill in the art, that such a known beat signal can be introduced, for example, by an apparatus that varies the relative optical pathlength difference between the optical pathlength traveled by radiation output from optical paths $2625_2, \ldots, 2625_n$ and the optical pathlength traveled by the radiation output from optical paths $2645_1, 2645_2, \ldots, 2645_n$. This can be done, for example, by using a frequency modulator (not shown in FIG. 1) in any one of a number of positions where it can provide the above-described function. Embodiments of such a frequency modulator can be fabricated in a number of different ways including those which are known to those of ordinary skill in the art. For example, a frequency modulator can be fabricated using movable reflector apparatus, apparatus wherein piezoelectric effects are used to vary a pathlength, apparatus using Bragg diffraction, apparatus using acousto-optic modulators, and any combination of the foregoing. Thus, whenever the term frequency modulator is used herein, it is meant to be used in its most general and inclusive sense.

In a preferred embodiment of the present invention, coherence processors $2070_1, 2070_2, \ldots, 2070_n$ are fabricated in accordance with a balanced heterodyne detection method described in an article entitled "Optical Reflectometry with Micrometer Resolution for the Investigation of Integrated Optical Devices" by P. Beaud, J. Schütz, W. Hodel, H. P. Weber, H. H. Gilgen and R. P. Salthé, IEEE J. Quantum Electronics, Vol. 25, No. 4, April 1989, pp. 755–759 (the "Beaud article"), which article is incorporated by reference herein. As described in the Beaud article, in accordance with the balanced heterodyne detection method, a second interference signal which is exactly 180° out of phase with respect to a first interference signal is introduced. Then, in accordance with this method, subtraction of these two phase-opposite interference signals suppresses noise associated with the system. As should be understood by those of ordinary skill in the art, each of coherence processors $2070_1, 2070_2, \ldots, 2070_n$ yields both the magnitude and relative phase of a coherent interference between its inputs when the time dependence introduced by the known beat signal is removed. These magnitudes and relative phases will be referred to below as "tomographic amplitudes." Advantageously, in accordance with a preferred embodiment of the present invention, coherence processors $2070_1, 2070_2, \ldots, 2070_n$ operate simultaneously to provide parallel processing so that n data points are collected simultaneously from one pulse output from SBRS 2010. Thus, whenever the term coherence processor is used herein, it is meant to be used in its most general and inclusive sense.

Next, as shown in FIG. 1, the tomographic amplitudes output from coherence processors $2070_1, 2070_2, \ldots, 2070_n$ are input to Fourier processor 2080. Fourier processor 2080 performs a Fourier transformation on the tomographic amplitudes by use of any one of a number of methods that are known to those of ordinary skill in the art, for example, by use of known Fast Fourier Transform (FFT) techniques. Thus, whenever the term Fourier processor is used herein, it is meant to be used in its most general and inclusive sense. The output of the Fourier transformation represents the spatial structure of the sample. That is, the Fourier transformation transforms the frequency dependence of the tomographic amplitudes to a spatial dependence, which spatial dependence describes spatial variations in depth (along the direction of propagation of the superbroad inspection radiation applied as input to the sample) as probed by the output from SBRS 2010 of FIG. 1. As those of ordinary skill in the art will readily appreciate, in accordance with the present invention, the pathlengths for all the beams (including the scattered inspection radiation from sample 2030 and reference radiation) to the respective coherence processors should to be the same, to within the coherence length of the superbroad inspection radiation output from SBRS 2010.

Finally, as shown in FIG. 1, the output from Fourier processor 2080 is transmitted to analysis/display apparatus 2090. Analysis/display apparatus 2090 is an apparatus for displaying images collected from sample 2030 as well as for analyzing the structure of sample 2030. There are many ways known to those of ordinary skill in the art for displaying such images and for analyzing the structure of sample 2030. For example, the images may be displayed on a video screen with predetermined densities of tissue indicated in false color and so forth. The sample analysis includes, for example, identifying predetermined structures on the basis of scattering intensity and the like. In one specific case, without intending to be limiting, tissues in a human eye can be identified by analysis of intensity levels of amplitudes at varying relative depths in the eye. In addition, it is included within the present invention to have analysis/display apparatus 2090 have the capability, in accordance with methods that are known to those of ordinary skill in the art, to accept input information, either from apparatus such as computers or directly from an operator to direct, for example, the activities of inspection apparatus 2000 in the sense of varying the portions of sample 2030 that are examined. Thus, whenever the term analysis/display apparatus is used herein, it is meant to be used in its most general and inclusive sense.

FIG. 11 shows, in pictorial form, spectrum separator 200 which divides an input beam into multiple output beams in accordance with the contents of the frequency spectrum of the input beam for use in fabricating embodiments of the present invention shown. In particular, a spectrum separator changes the coherence of the input beam, i.e., the coherence becomes higher for the output beams since the spectral widths of the output beams are narrower. As shown in FIG. 11, radiation is output from optical path 101 at the back focal plane of lens system 210. Beam 211 is output from lens system 210 and is comprised of parallel rays. Next, beam 211 is applied as input to diffraction grating 220 and beams 221 and 222 which are output by diffraction grating 220: (a) are each comprised of parallel rays, (b) have frequency spectra substantially centered at different frequencies, and (c) are directed away from diffraction grating 220 at different angles. Next, beams 221 and 222 impinge upon focusing lens system 230 and are output as focused beams 231 and 232, respectively. Focused beams 231 and 232 impinge upon different portions of focal plane 240 of lens system 230 in accordance with the contents of their frequency spectrum in a well known manner. As further shown in FIG. 11, an optical path assembly 250 is comprised of a multiplicity of optical paths $250_1, 250_2, 250_n$. It is noted that the term optical path, as was mentioned above, is used in its most general sense. As those of ordinary skill in the art will readily appreciate, in designing an inspection apparatus in accordance with the present invention, it is important to take into account the optical pathlength of each optical path as well as optical pathlength differences that occur. Thus, a preferred embodiment minimizes optical pathlength delays introduced by optical paths, optical couplers, and the like within spectrum separator 200. Further, the preferred spectrum separator minimizes these optical pathlength delays, and does not introduce optical pathlength differences among different optical paths. As those of ordinary skill in the art should further appreciate, the optical paths, optical couplers, and the like may be integrated to form a chip to reduce the size and cost of spectrum separator 200.

In a further embodiment of spectrum separator 200 for use in fabricating embodiments of the present invention, spectrum separator 200 includes launching assembly 217 (shown pictorially by dotted lines) that is movable in a direction indicated by double arrow 215. The movement of launching assembly 217 provides a common, continuously variable, optical pathlength delay for all beams output from spectrum separator 200. Many methods and apparatus (not shown) for moving launching assembly 217 are known to those of ordinary skill in the art. Thus, whenever the term apparatus for moving a launching assembly is used herein, it is meant to be used in its most general and inclusive sense. The main function of the movement of launching assembly 217 is to vary the optical pathlength to provide longitudinal scanning in the sample, i.e., a common, variable, optical pathlength delay provides a mechanism for scanning in the direction of the incident inspection radiation (in depth in the sample). Mechanical movement may be slow and may be unstable in some instances. Therefore, in a preferred embodiment, launching assembly 217 is fixed and a variable, optical pathlength delay network is inserted into optical path 101 to vary the optical pathlength. As those of ordinary skill in the art can readily appreciate, the replacement of a moving mechanism for providing longitudinal scanning by a variable delay network can advantageously increase the inspection speed. A variable, optical pathlength delay network can be fabricated in a number of ways that are well known to those of ordinary skill in the art. For example, see an article entitled "Photonic Wideband Array Antennas" by J. J. Lee, R. Y. Loo, S. Livingston, V. I. Jones, J. B. Lewis, H-W. Yen, G. L. Tangonan and M. Wechsberg, *IEEE Trans. On Antenna and Propagation*, Vol. 43, No. 9, September 1995, pp. 966–982. This article is incorporated by reference herein and describes a variable optical pathlength device having 32 preset delays. In addition, see chapter 13 of a book entitled "Photonic Aspects of Modem Radar," edited by H. Zmuda and E. N. Toughlican, published by *Artech House,* 1994, chapter 13 being entitled "Switched Fiber-Optic Delay Architectures" by A. P. Goutzoulis and D. K. Davies, pp. 351–380, the chapter being incorporated by reference herein. The chapter described several embodiments of switched, fiber optic delay lines. Lastly see an article entitled "A Hardware Compressive Fiber-Optic True Time Delay Steering System for Phase-Array Antennas" by A. Goutzoulis, K, Davis, J. Zomp, P. Hrycak and A. Johnson, *Microwave J.*, September 1994, pp. 126–140, which article is incorporated by reference herein.

Figure 12:
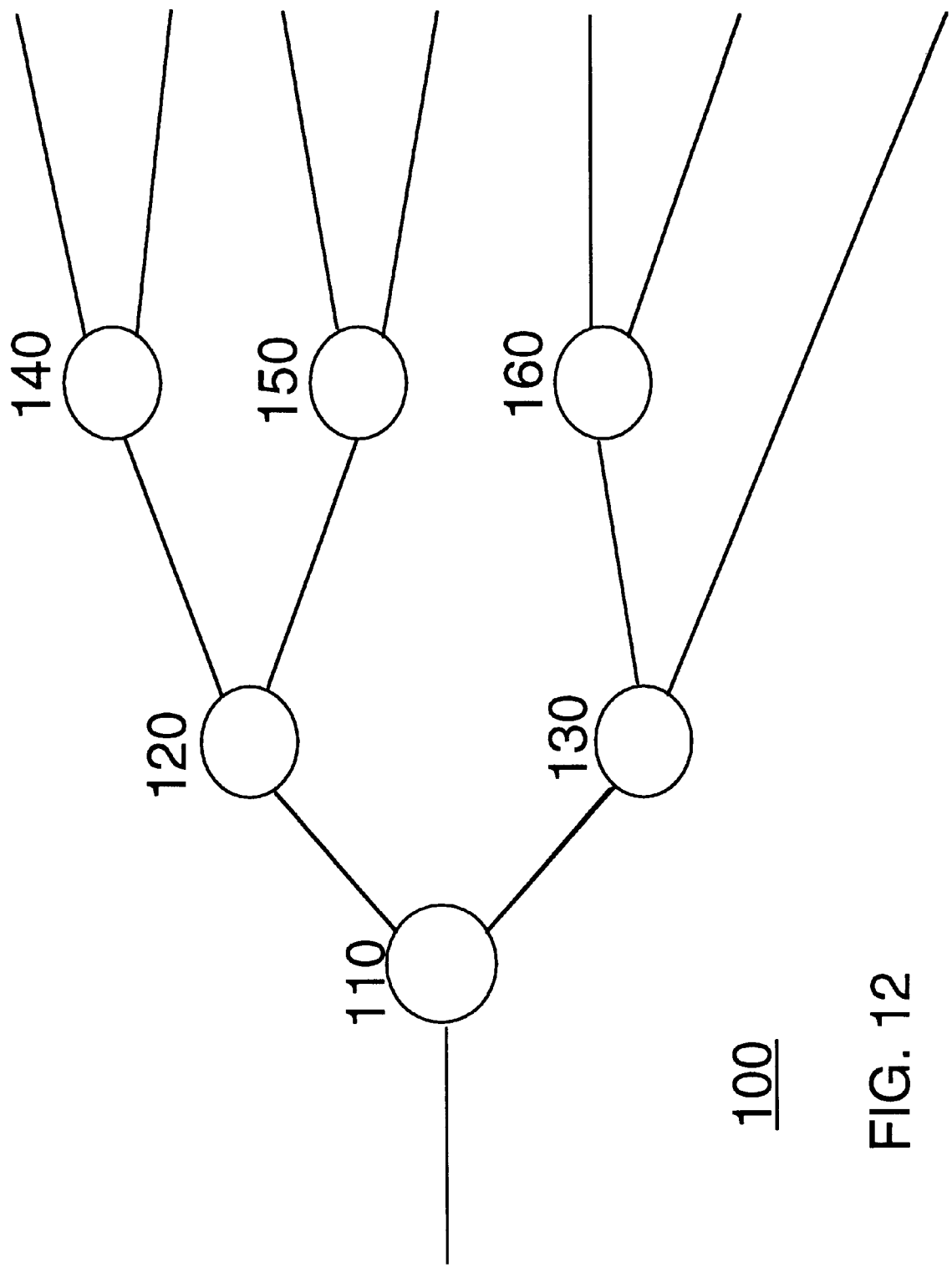
FIG. 12 shows, in pictorial form, a beam divider that is used to fabricate embodiments of the present invention.

In a still further embodiment of spectrum separator 200, instead of using a grating, spectrum separator 200 is fabricated using a beam divider, such as for example, beam divider 100 shown in FIG. 12, together with band-limited filters. In this embodiment of spectrum separator 200, the band-limited filters provide the finction of partitioning the frequency spectrum of input beam 101. Band-limited filters are fabricated in accordance with many methods known to those of ordinary skill in the art.

In a yet still further embodiment of spectrum separator 200, spectrum separator 200 is comprised of an assembly of spectrum separators. For example, in one such embodiment, each of the spectrum separators is comprised of one or more frequency demultiplexors, for example, a grating. Thus, whenever the term spectrum separator is used herein, it is meant to be used in its most general and inclusive sense.

FIG. 12 shows, in pictorial form, beam divider 100 which divides an input beam into multiple output beams for use in fabricating embodiments of the present invention. In particular, a beam divider does not change the coherence of the input beam. As shown in FIG. 12, beam divider 100 comprises couplers 110, 120, 130, 140, 150, and 160, each of which couplers splits an input optical path into two output optical paths. As those of ordinary in the art should readily appreciate, many different and varied embodiments of beam dividers can be used to fabricate embodiments of the present invention and, as such, beam divider 100 shown in FIG. 12 is shown for illustrative purposes only. It is noted that the term optical path, as was mentioned above, is used in its most general sense. A preferred beam divider has low loss and, depending on the differences in power in the various frequency bands, advantageously provides output beams having substantially equal power. As those of ordinary skill in the art can readily appreciate, in designing an inspection apparatus in accordance with the present invention, it is important to take into account the optical pathlength of each optical path as well as optical pathlength differences that occur between different outputs. Thus, a preferred beam divider minimizes optical pathlength delays introduced by optical paths, optical couplers, and the like within beam divider 100. Further, the preferred beam divider minimizes these optical pathlength delays, and does not introduce optical pathlength differences among different optical paths. As those of ordinary skill in the art should further appreciate, the optical paths, optical couplers, and the like may be integrated to form a chip to reduce the size and cost of beam divider 100. Thus, whenever the term beam divider is used herein, it is meant to be used in its most general and inclusive sense.

Figure 13:
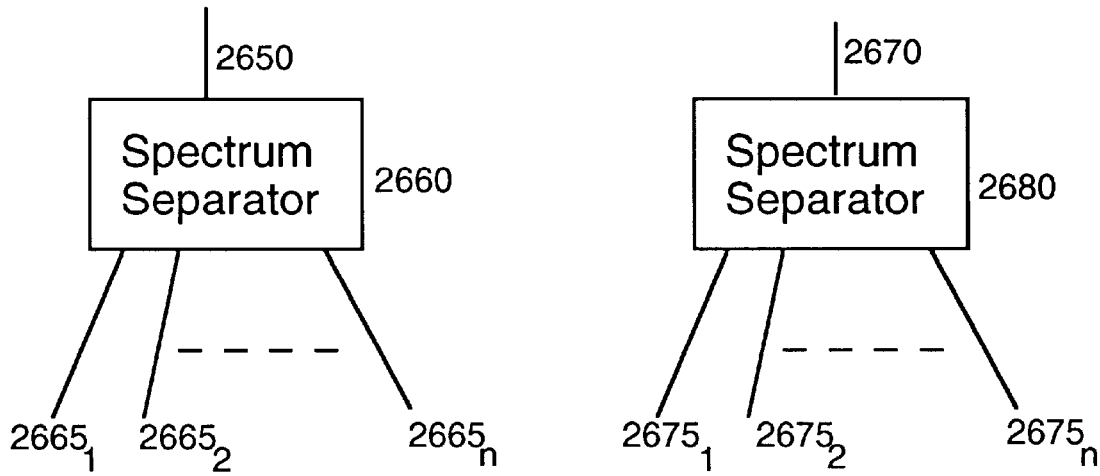
FIGS. 13–14 show block diagrams of dispersal apparatus that are used to fabricate embodiments of the first aspect of the present invention.

FIG. 13 shows, in pictorial form, a further embodiment of a dispersal apparatus for use in fabricating embodiments of the present invention, for example, embodiments shown in FIG. 1. As shown in FIG. 13, superbroad reference radiation output from optical path 2650 is applied as input to spectrum separator 2660 and scattered inspection radiation output from optical path 2670 is applied as input to spectrum separator 2680. Spectrum separator 2660 divides the radiation applied as input from optical path 2650 into multiple beams in accordance with the contents of the frequency spectrum of the radiation and applies the multiple beams, in turn, as inputs to optical paths $2665_1, 2665_2, \ldots, 2665_n$, respectively. Spectrum separator 2670 divides the radiation applied as input from optical path 2670 into multiple beams in accordance with the contents of the frequency spectrum of the input radiation and applies the multiple beams, in turn, as inputs to optical paths $2675_1, 2675_2, \ldots, 2675_n$, respectively. Usually a spectrum separator has larger losses than a beam divider. However, if such losses are not a problem, the replacement of the beam divider of the embodiment shown in FIG. 10 with a spectrum separator will reduce cross contamination that may occur among the main and side lobes of different beams output from spectrum separator 200 of FIG. 11.

Figure 14:
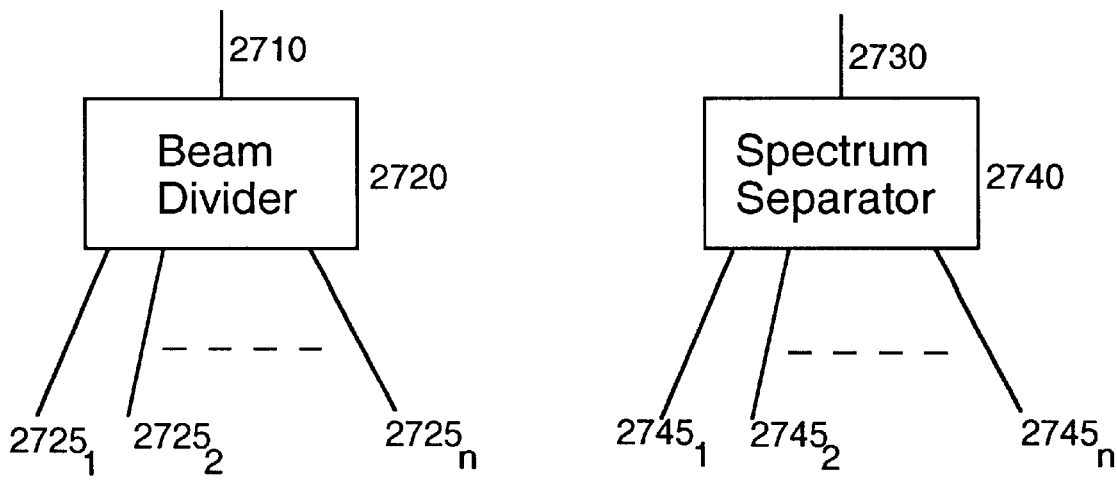

FIG. 14 shows, in pictorial form, a still further embodiment of a dispersal apparatus for use in fabricating embodiments of the present invention, for example, embodiments shown in FIG. 1. As shown in FIG. 14, superbroad reference radiation output from optical path 2710 is applied as input to beam divider 2720 and scattered inspection radiation output from optical path 2730 is applied as input to spectrum separator 2740. Beam divider 2720 divides the radiation applied as input from optical path 2720 into multiple beams and applies the multiple beams, in turn, as inputs to optical paths $2725_1, 2725_2, \ldots, 2725_n$, respectively. Spectrum separator 2740 divides the radiation applied as input from optical path 2730 into multiple beams in accordance with the contents of the frequency spectrum of the radiation output from optical path 2730 and applies the multiple beams, in turn, as inputs to optical paths $2745_1, 2745_2, \ldots, 2745_n$, respectively.

In addition to the above, an embodiment of a dispersal apparatus for use in connection with an embodiment of a superbroad radiation source like that shown in FIG. 6 which produces a multiplicity of reference radiation outputs over optical paths $2260_1, 2260_2, \ldots, 2260_n$ may be fabricated by using the optical paths $2260_1, 2260_2, \ldots, 2260_n$ together with either a spectrum separator or a beam divider to provide multiple radiation outputs from the scattered inspection radiation. In addition, each of the reference radiation outputs may also be transmitted through a spectrum separator to provide a better quality of separation in the frequency spectra of the multiple reference radiation outputs.

We now return to inspection apparatus 2000 shown in FIG. 1. As was described above, in accordance with the present invention, inspection apparatus 2000 advantageously utilizes parallel processing to provide high speed, high precision inspection. As was also described above, the width of the frequency spectrum of at least one of the radiation inputs to each of coherence processors $2071_1, 2071_2, \ldots, 2071_n$ by dispersal apparatus 2050 is less than the width of the frequency spectrum of the superbroad inspection radiation output from SBRS 2010. Since a narrower spectral width provides a higher coherence, these radiation inputs have higher coherence than the inspection radiation.

Because radiation coherence directly affects the spatial depth probed by inspection apparatus 2000, a difference in coherence among the higher coherence radiation inputs to coherence processors $2071_1, 2071_2, \ldots, 2071_n$ would lead to a variation in spatial depth probed. Thus, in preferred embodiments of the present invention, the widths of the frequency spectra of the higher coherence radiation inputs to coherence processors $2071_1, 2071_2, \ldots, 2071_n$ are substantially the same to provide uniformity in spatial depth probed by each of the inputs. This is advantageous since it helps to suppress unwanted system variations.

In accordance with the present invention, the spatial resolving power of inspection apparatus 2000 is mainly determined by the coherence length of the superbroad inspection radiation output from SBRS 2010. Further, the spatial depth probed by inspection apparatus 2000 in sample 2030 is mainly determined by the widths of the frequency spectra of the higher coherence radiation inputs to coherence processors $2071_1, 2071_2, \ldots, 2071_n$. In fact, in the preferred embodiment, the spatial depth probed by inspection apparatus 2000 is substantially given by the product of the coherence length of the superbroad inspection radiation output from SBRS 2010 and the ratio of the width of the frequency spectrum of the superbroad inspection radiation output from SBRS 2010 and the width of the frequency spectrum of the higher coherence radiation inputs to $2071_1, 2071_2, 2071_3, \ldots, 2071_n$. Hence, the resolving power of inspection apparatus 2000 is comparable to that provided by a conventional OCT interferometer in the prior art, but the number, n, of the multiple higher coherence radiation inputs to coherence processors $2071_1, 2071_2, \ldots, 2071_n$ indicates how many independent measurements would be needed using a conventional OCT interferometer in the prior art to replicate the results provided by one output pulse using inventive inspection apparatus 2000. Thus, n also indicates the time savings multiplier that results in forming a tomographic image using inventive inspection apparatus 2000.

We note one problem that can occur with certain embodiments of the present invention. This problem is caused by the use of a spectrum separator that produces multiple output beams having undesirable deviations. First, the frequency spectrum widths are so small that "undersampling" occurs. Second, spectrum widths radiation intensities, and pathlengths of these output beams are not uniform. "Undersampling" produces spatial ambiguity and contamination of an image at one spatial location with image components from multiple spatial locations. A way to solve the "undersampling" problem is to increase the frequency width of the superbroad radiation and the multiplicity of output beams or to decrease the spatial region probed by the apparatus. Nonuniformity produces tomographic image blurring. Through adjustments of spectrum width, intensity, and pathlength among different channels, one can eliminate or minimize nonuniformity problems.

Figure 15:
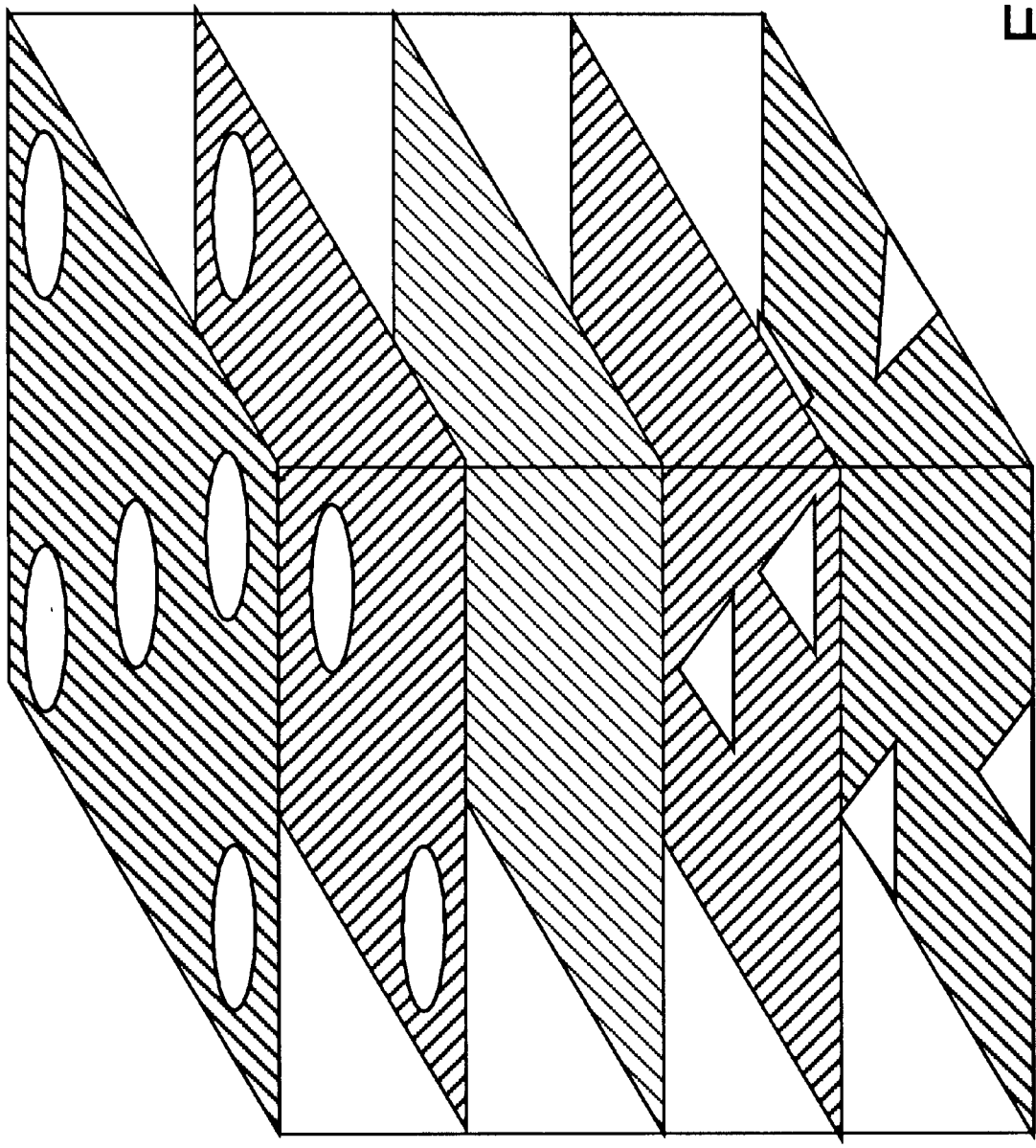
FIG. 15 shows, in pictorial form a calibration apparatus that is used to calibrate certain embodiments of the present invention.

FIG. 15 shows, in pictorial form, calibration apparatus 400 which is used with embodiments of the present invention to resolve undesirable deviations. A calibration apparatus is a man made object which has well known geometrical structures and physical properties. An inventive inspection apparatus will use the calibration apparatus to produce tomographic images. Then, by comparing the measured tomographic images with the known structures of the calibration apparatus, one can identify system undesirable deviations and take measures to remove them. Calibration apparatus 400 depicted in FIG. 15 is for illustrative purposes only and many different kinds of calibration apparatus may be fabricated in accordance with the present invention.

In some embodiments of the present invention, it is possible to skip an undesirable frequency channel due to high losses, or to reduce the number of channels n at the expense of a predetermined degradation in the quality of the tomographic images. This results in broadening the superbroad inspection radiation or in costs savings involved in setting up parallel channels. The skipping or reduction may be done in accordance with techniques of array thinning such as that set forth in a book entitled "Interferometry and Synthesis in Radio Astronomy" by A. R. Thompson et al., p. 126, *Krieger Publishing Company*, 1991, and in another book entitled "Practical Phased-Array Antenna Systems" edited by Eli Brookner, p. 2–27, *Artech House,* 1991. The reference books are incorporated by reference herein.

The following describes specific embodiments of the present invention in accordance with the embodiment of the first aspect of the present invention shown in FIG. 1.

Figure 16:
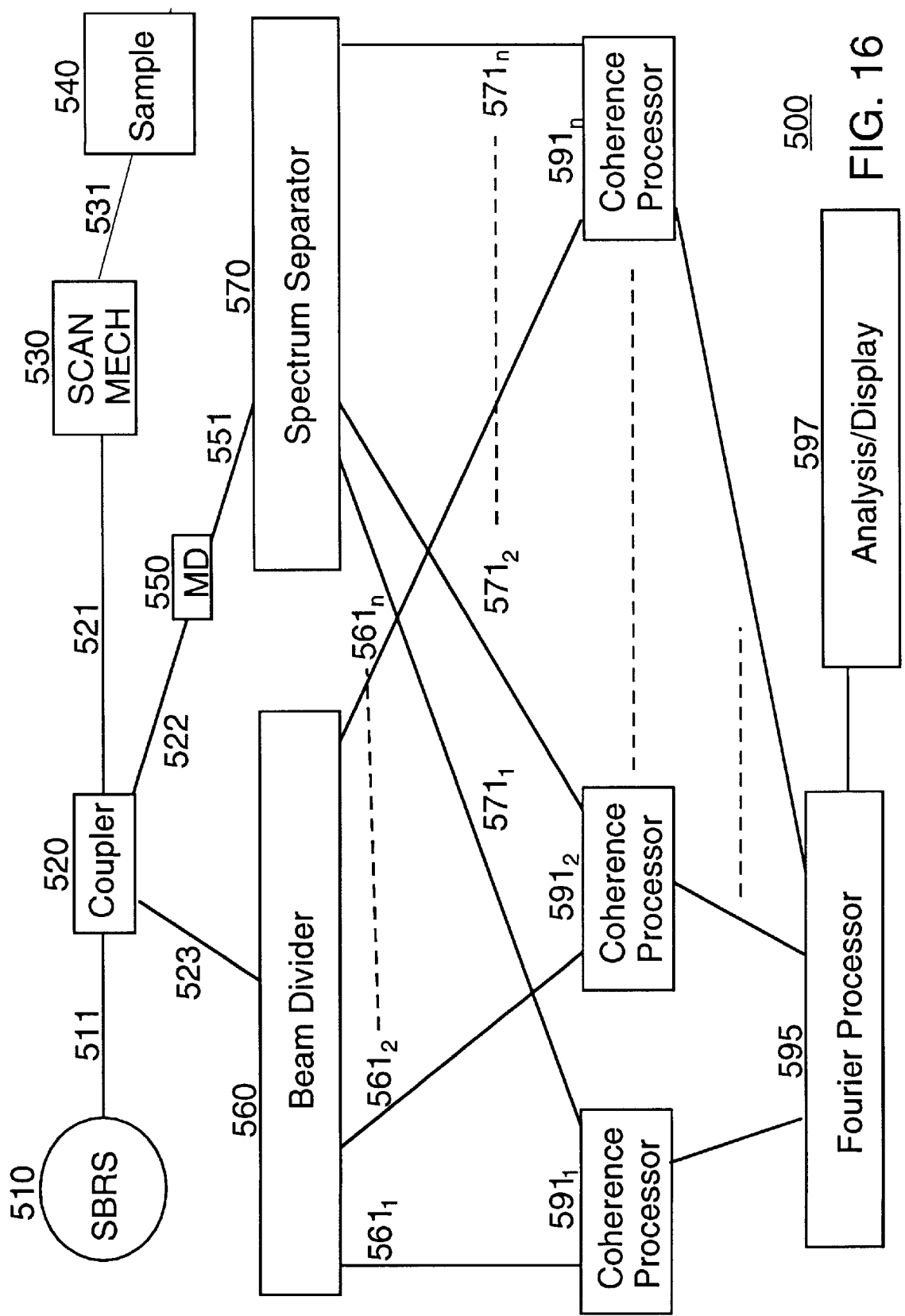
FIGS. 16–17 show block diagrams of inspection apparatus that are fabricated in accordance with the first aspect of the present invention.

FIG. 16 shows a block diagram of inspection apparatus 500 that is fabricated in accordance with the first aspect of the present invention. As shown in FIG. 1, inspection apparatus 500 includes SBRS 510 (for example, a low coherence radiation source) which outputs superbroad coherence radiation that is applied as input to optical path 511. The superbroad radiation output from optical path 511 is applied, in turn, as input to coupler 520. Next, coupler 520 applies a first portion of the input superbroad radiation as superbroad inspection radiation input to optical path 521 and applies a second portion of the input superbroad radiation as superbroad reference radiation input to optical path 522.

The superbroad inspection radiation output from optical path 521 is applied as input to scanning apparatus 530. Scanning apparatus 530 scans the superbroad inspection radiation applied as input from optical path 521 in a transverse direction, over optical path 531, across sample 540, for example a human eye. Inspection radiation that is backscattered from sample 540 is applied as input to optical path 531. Next, the backscattered inspection radiation output from optical path 531 is applied as input to scanning mechanism 530, and scanning mechanism 530, in turn, applies the backscattered inspection radiation as input to optical path 521. Next, backscattered inspection radiation output from optical path 521 is applied as input to coupler 520 and coupler 520, in turn, applies the backscattered inspection radiation as input to optical path 523. Next, the backscattered inspection radiation output from optical path 523 is applied as input to beam divider 560.

The superbroad reference radiation output from optical path 522 is applied as input to optional frequency modulator MD 550. MD 550 is optional and its use in fabricating an embodiment of this first aspect of the present invention, if at all, will be explained in detail below. Superbroad reference radiation output from optional frequency modulator MD 550 is applied as input to optical path 551, and the superbroad reference radiation output from optical path 551 is applied, in turn, as input to spectrum separator 570. It should be understood by those of ordinary skill in the art that if MD 550 is not used, there is preferably a single optical path which transports the superbroad reference radiation from coupler 520 to spectrum separator 570.

Spectrum separator 570 divides the superbroad reference radiation output from optical path 551 into multiple beams in accordance with the contents of the frequency spectrum of the superbroad reference radiation and applies the multiple beams as inputs to optical paths $571_1, 571_2, \ldots, 571_n$, respectively. The center frequency and width of the frequency spectrum of each of the multiple beams output from spectrum separator 570, as was described above, are determined by the center and width of its corresponding frequency spectrum window at spectrum separator 570. As those of ordinary skill in the art should readily appreciate, the difference between the highest and lowest center frequencies of the frequency spectra of the multiple beams is limited by the width of the frequency spectrum of the superbroad radiation output from SBRS 510.

Beam divider 560 divides the backscattered inspection radiation output from optical path 523 into multiple beams and applies the multiple beams as inputs to optical paths $561_1, 561_2, \ldots, 561_n$. The useful number of multiple beams that beam divider 560 can provide depends on the intensity of the backscattered inspection radiation output from optical path 523. The intensity of the backscattered inspection radiation output from optical path 523 is usually lower than the intensity of the superbroad reference radiation output from optical path 551. If necessary in a particular embodiment, this difference in intensity can be overcome, in principle, by appropriately amplifying the backscattered inspection radiation output by use of optical amplifiers in any one of a number of places, for example, in optical paths 521 or 523. Alternatively, one or more of the multiple beams applied as input to optical paths $561_1, 561_2, \ldots, 561_n$ may be amplified also (or instead of amplification in one or more of optical paths 521 and 523). Further, as will become apparent from the further discussion below, one or more of the multiple beams that are applied as input to optical paths $561_1, 561_2, \ldots, 561_n$ may advantageously be amplified in narrow frequency bands.

As shown in FIG. 16, the radiation outputs from optical paths $561_1, 561_2, \ldots, 561_n$ and the radiation outputs from optical paths $571_1, 571_2, \ldots, 571_n$ are applied, pairwise respectively, to coherence processors $591_1, 591_2, \ldots, 591_n$ respectively. Coherence processors $591_1, 591_2, \ldots, 591_n$ utilize optical heterodyne techniques that are known to those of ordinary skill in the art to measure coherent interference between radiation output from optical paths $561_1, 561_2, \ldots, 561_n$ formed from the backscattered inspection radiation and radiation output from optical paths $571_1, 571_2, \ldots, 571_n$. However, as is known to those of ordinary skill in the art, the optical heterodyne techniques produce many non-coherent outputs along with the coherent interference outputs. As is also known to those of ordinary skill in the art, a known beat signal can be used to enhance detection of the coherent interference outputs in the presence of the non-coherent outputs. It is also known to those of ordinary skill in the art, that such a known beat signal can be introduced, for example, by an apparatus that varies the relative optical pathlength difference between the optical pathlength traveled by radiation output from optical paths $561_1, 561_2, \ldots, 561_n$ and the optical pathlength traveled by the radiation output from optical paths $571_1, 571_2, \ldots, 571_n$ This can be done by using frequency modulator MD 550 shown in FIG. 16. FIG. 16 shows frequency modulator MD 550 located at one of the many positions it can be positioned to provide the above-described function. As those of ordinary skill in the art will readily appreciate, MD 550 can also be placed in one or more of optical paths 521 and 523.

In a preferred embodiment of the present invention, coherence processors $591_1, 591_2, \ldots, 591_n$ are fabricated in accordance with the balanced heterodyne detection method described in the Beaud article. As should be understood by those of ordinary skill in the art, each of coherence processors $591_1, 591_2, \ldots, 591_n$ yields both the magnitude and relative phase of a coherent interference between its inputs when the time dependence introduced by the known beat signal is removed, i.e., the "tomographic amplitudes." Advantageously, in accordance with a preferred embodiment of the present invention, coherent processors $591_1, 591_2, \ldots, 591_n$ operate simultaneously to provide parallel processing so that n data points are collected simultaneously from one pulse output from SBRS 510.

Next, as shown in FIG. 16, the tomographic amplitudes output from coherence processors $591_1, 591_2, \ldots, 591_n$ are input to Fourier processor 595. Fourier processor 595 performs a Fourier transformation on the tomographic amplitudes. The output of the Fourier transformation represents the spatial structure of the sample. That is, the Fourier transformation transforms the frequency dependence of the tomographic amplitudes to a spatial dependence, which spatial dependence describes spatial variations in depth (along the direction of propagation of the superbroad inspection radiation applied as input to the sample) as probed by the output from SBRS 510 of inspection apparatus 500. As those of ordinary skill in the art will readily appreciate, in accordance with the present invention, the pathlengths for all the beams (including the backscattered inspection radiation from sample 540 and the multiple beams generated by beam divider 560 on one hand and the superbroad reference radiation output from coupler 520 and applied as input to optical path 522 and the multiple beams generated by spectrum separator 570) to the respective coherence processors should to be the same, to within the coherence length of the output radiation from SBRS 510. Finally, as shown in FIG. 16, the output from Fourier processor 595 is transmitted to analysis/display module 597. Analysis/display module 597 is an apparatus for displaying images collected from sample 540 as well as for analyzing the structure of sample 540.

As was described above, in accordance with the present invention, inspection apparatus 500 advantageously utilizes parallel processing to provide high speed, high precision inspection. As is known to those of ordinary skill in the art, the coherence of a beam of radiation depends on the content of its frequency spectrum. Further, as was described above, the frequency spectra of the multiple beams applied as input to optical paths $571_1, 571_2, \ldots, 571_n$ by spectrum separator 570 are subsets of the frequency spectrum of the superbroad reference radiation output from optical path 551, i.e., the frequency spectra of each of the multiple beams applied as input to optical paths $571_1$, $571_2$, ..., $571_n$ have narrower spectral widths than that of the superbroad reference radiation output from optical path 551. Since a narrower spectral width provides a higher coherence, the multiple beams applied as input to optical paths $571_1$, $571_2$, ..., $571_n$ have higher coherence than the beam input to spectrum separator 570 from optical path 551.

As is known to those of ordinary skill in the art, beam coherence directly affects the spatial depth probed by inspection apparatus 500 during a measurement. Further, a difference in coherence among the multiple beams applied as input to optical paths $571_1$, $571_2$, ..., $571_n$ would lead to a variation in spatial depth probed. Thus, in preferred embodiments of the present invention, the widths of the frequency spectra of the multiple beams applied as inputs to optical paths $571_1$, $571_2$, ..., $571_n$ are substantially the same to provide uniformity in spatial depth probed for each of the beams. This is advantageous since it helps to suppress unwanted system variations. The spatial resolving power of inspection apparatus 500 is mainly determined by the coherence length of the superbroad radiation output from SBRS 510. Further, the spatial depth probed by inspection apparatus 500 in sample 540 is mainly determined by the widths of the frequency spectra of the multiple beams applied as input to optical paths $571_1$, $571_2$, ..., $571_n$. In fact, in the preferred embodiment, the spatial depth probed by inspection apparatus 500 is substantially given by the product of the coherence length of the superbroad radiation output from SBRS 510 and the ratio of the width of the frequency spectrum of the superbroad radiation output from SBRS 510 and the width of the frequency spectrum of the multiple beams applied as input to optical paths $571_1$, $571_2$, $571_3$, ..., $571_n$. Hence, the resolving power of inspection apparatus 500 is comparable to that provided by a conventional OCT interferometer in the prior art, but the number, n, of the multiple beams applied as input to optical paths $571_1$, $571_2$, ..., $571_n$ indicates how many independent measurements would be needed using a conventional OCT interferometer in the prior art to replicate the results provided by one output pulse using inventive inspection apparatus 500. Thus, n also indicates the time savings multiplier that results in forming a tomographic image using inventive inspection apparatus 500.

Figure 17:
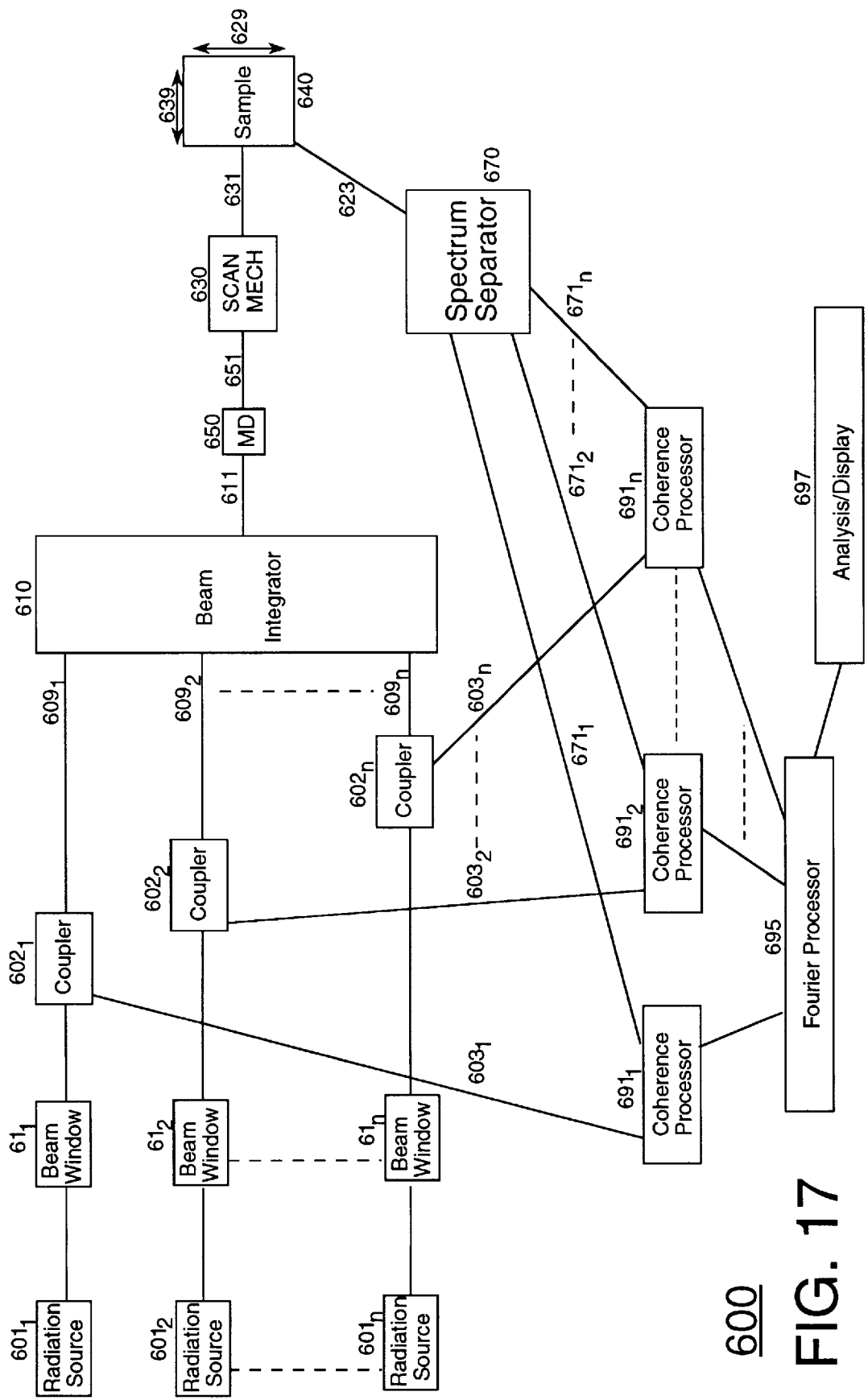

FIG. 17 shows a block diagram of inspection apparatus 600 that is fabricated in accordance with the first aspect of the present invention. As shown in FIG. 17, inspection apparatus 600 includes a multiplicity of radiation sources $601_1$, $601_2$, ..., $601_n$ which output radiation that is applied over an optical path as input to beam windows $61_1$, $61_2$, ..., $61_n$, respectively. Each of beam windows $61_1$, $61_2$, ..., $61_n$ adjusts the pulse width, and hence the frequency spectrum, of radiation output from radiation sources $601_1$, $601_2$, ..., $601_n$, respectively, to predetermined widths.

The output from beam windows $61_1$, $61_2$, ..., $61_n$, respectively, are applied over optical paths as input to couplers $602_1$, $602_2$, ..., $602_n$, respectively. Couplers $602_1$, $602_2$, ..., $602_n$, respectively, apply a first portion of the input radiation as input to optical paths $609_1$, $609_2$, ..., $609_n$, respectively, and apply a second portion of the input radiation as input to optical paths $603_1$, $603_2$, ..., $603_n$, respectively. The radiation outputs from optical paths $609_1$, $609_2$, ..., $609_n$ are applied as input to beam integrator 610. Beam integrator 610 combines the radiation applied as input from optical paths $609_1$, $609_2$, ..., $609_n$ into a single beam of superbroad inspection radiation and applies the single beam of superbroad inspection radiation as input to optical path 611. A preferred embodiment of beam integrator 610 has low loss so that it will attenuate only a small amount of the power of the input radiation.

Next, the superbroad inspection radiation output from optical path 611 is applied as input to optional frequency modulator MD 650. Superbroad inspection radiation output from optional frequency modulator MD 650 is applied as input to optical path 651. Next, the superbroad inspection output from optical path 651 is applied as input to optional scanning apparatus 630. Scanning mechanism 630 may be omitted, or used in part, and some of the role, if not all of the role, played by scanning apparatus 630 is provided by a sample moving apparatus (not shown) that moves sample 640 in one or more of three dimensions, including one or both of the directions indicated by arrows 629 and 639, respectively. The sample moving apparatus can be, for example, a movable table top on which sample 640 is disposed. It should be understood by those of ordinary skill in the art that if MD 650 is not used, there is preferably a single optical path which transports the superbroad inspection radiation from beam integrator 610 to scanning mechanism 630.

Next, scanning mechanism 630 scans the superbroad radiation applied as input from optical path 651 in a transverse direction over optical path 631 across sample 640. Inspection radiation that is scattered from sample 640 is applied as input to optical path 623. Next, the scattered inspection radiation output from optical path 623 is applied as input to spectrum separator 670. Spectrum separator 670 separates the superbroad scattered inspection radiation output from optical path 623 into multiple beams and applies the multiple beams as input to optical paths $671_1$, $671_2$, ..., $671_n$, respectively. The center frequency and width of the frequency spectrum of each of the multiple beams output from spectrum separator 670 are determined by the center and width of its respective frequency spectrum window at spectrum separator 670. Advantageously, in accordance with this embodiment of the first aspect of the present invention, the difference between the highest and lowest center frequencies of the multiple beams is determined by the difference between the highest and lowest center frequencies of the radiation output from the multiplicity of radiation sources $601_1$, $601_2$, ..., $601_n$.

As shown in FIG. 17, the radiation outputs from optical paths $603_1$, $603_2$, ..., $603_n$ and from optical paths $671_1$, $671_2$, ..., $671_n$ are applied, pairwise respectively, as inputs to coherence processors $691_1$, $691_2$, ..., $691_n$, respectively. Note that, reference and scattered radiation that are paired at each coherence processor in FIG. 17 originate from a single radiation source, i.e., optical pathlengths for each pair of radiation inputs to a coherence processor, measured from their respective splitting coupler to the coherence processor, should be substantially the same. As is well known to those of ordinary skill in the art, to enhance the detection of the coherent interference output in the presence of the non-coherent output, a known beat signal is used. As was described above, such a beat signal can be introduced, for example, by an arrangement that varies the relative optical pathlength between the optical pathlength of the multiple beams output from optical paths $603_1$, $603_2$, ..., $603_n$ and the optical pathlength of the multiple beams output from optical paths $671_1$, $671_2$, ..., $671_n$. Frequency modulator MD 650 is shown in FIG. 17 in one of the many positions it can be placed to provide the above-described function. As those of ordinary skill in the art will readily appreciation, MD 650 can also be placed in one or more of the optical paths to provide this function.

In a preferred embodiment of the present invention, coherence processors $691_1, 691_2, \ldots, 691_n$ are fabricated in accordance with the balanced heterodyne detection scheme described above in the Beaud article to yield tomographic amplitudes. Advantageously, in accordance with a preferred embodiment of the present invention, coherence processors $691_1, 691_2, \ldots, 691_n$ operate simultaneously to provide parallel processing so that n data points are collected simultaneously from one pulse output from multiple radiation sources $601_1, 601_2, \ldots, 601_n$. Next, as shown in FIG. 17, the tomographic amplitudes output from coherence processors $691_1, 691_2, \ldots, 691_n$ are input to Fourier processor 695 which operates in the manner described above to perform a Fourier transformation on the tomographic amplitudes to transform the frequency dependence of the tomographic amplitudes to a spatial dependence, which spatial dependence describes spatial variations in depth as probed by the superbroad radiation output from multiple radiation sources $601_1, 601_2, \ldots, 601_n$ of inspection apparatus 600. As those of ordinary skill in the art will readily appreciate, in accordance with the present invention, the optical pathlengths for all the beams (including scattered radiation from sample 640 and the multiple beams generated by the relevant portions of inspection apparatus 600) ought to be the same to within the coherence length of the radiation output from multiple radiation sources $601_1, 601_2, \ldots, 601_n$. Finally, as shown in FIG. 17, the output from Fourier processor 695 is transmitted to analysis/display module 697.

It should be understood that alternative embodiments of inspection apparatus 600 can be fabricated by utilizing a single spectrum separator or a multiplicity of spectrum separators to receive the outputs from optical paths $603_1, 603_2, \ldots, 603_n$ prior to applying them to coherence processors $691_1, 691_2, \ldots, 691_n$ to further tailor the frequency spectra. Of course such an embodiment can be used with or without beam windows $61_1, 61_2, \ldots, 61_n$. In a further embodiment, a multiplicity of spectrum separators can be utilized to provide multiple output channels. In this case, the spectrum separators can be arranged as follows. Assume, for the sake of this example, that the superbroad radiation is to be separated into 100 channels. This is done by using a first spectrum separator to separate the incident superbroad radiation into ten (10) channels. Then, this is followed by using ten (10) additional spectrum separators in each of the first ten channels, in parallel, to separate each of the 10 channels into 10 channels each.

Inspection apparatus 600, and the use of multiple, independent radiation sources, can advantageously lead to larger frequency variations and better resolution than that provided by a single radiation source. In one way of understanding the operation of inspection apparatus 600, it may be considered to be a coherently integrated interferometer apparatus which is comprised of many apparatus like inspection apparatus 500 shown in FIG. 16.

It is recommended to take the following into account when fabricating inspection apparatus 600 to best utilize the teaching of the present invention. First, it is advantageous to provide uniform spatial gating for the inspection channels (the pulse width of each beam of radiation input to beam integrator 610 determines the spatial gating for the inspection channels). Further, since radiation sources $601_1, 601_2, \ldots, 601_n$ include low coherence sources, pulsed sources, and continuous sources, the specific method and apparatus used to provide spatial gating depends on the nature of the sources used in a particular embodiment. For example, a spectrum separator may be used to provide a predetermined spatial gating for a low coherence radiation source, but not for continuous sources. This is because a typical spectrum separator is used to lengthen the width of a pulse and not to reduce it. Further, a beam window may be used to provide a predetermined spatial gating for a continuous source (a typical continuous source outputs radiation having a higher than desired coherence) because a typical beam window is used to narrow the width of a pulse. In a particular embodiment, whether or not beam windows are used depends on the frequency spectrum of the radiation output from specific ones of the sources. Thus, in further alternative embodiments of the present invention, some or all of beam windows $61_1, 61_2, \ldots, 61_n$ may be omitted for radiation sources that output radiation having the desired frequency spectrum. Second, when counting optical pathlengths for all scattered radiation, the optical pathlengths must be referred to the same point in sample 640.

The following is a description of an embodiment of a second aspect of the present invention, which description provides a broad overview of the second aspect of present invention.

FIG. 2 shows a block diagram of inspection apparatus 3000 that is fabricated in accordance with the second aspect of the present invention. As shown in FIG. 2, inspection apparatus 300 includes superbroad radiation source 3010 ("SBRS 3010") which outputs superbroad inspection radiation 3015 having a frequency spectrum with a frequency width that will be referred to below as an inspection width. SBRS 3010 outputs superbroad inspection radiation 3015 and applies it as input to inspection applicator apparatus 3020, and inspection applicator apparatus 3020, in turn, applies inspection radiation 3025 as input to sample 3030. Next, inspection collection apparatus 3040 collects at least a portion of the inspection radiation that is scattered by sample 3030 (scattered inspection radiation 3035), and inspection collection apparatus 3040, in turn, applies scattered inspection radiation 3045 as input to dispersal apparatus 3050.

As is also shown in FIG. 2, SBRS 3010 outputs superbroad reference radiation 3017 and applies it as input to reference collection and delay apparatus 3060. Reference collection and delay apparatus 3060 produces a predetermined number of superbroad reference radiation outputs 3065 having predetermined delays with respect to one another and applies the reference radiation outputs 3065 as input to dispersal apparatus 3050.

Next, dispersal apparatus 3050 applies radiation from scattered inspection radiation 3045 as input to coherence processor 3070 and applies radiation from the reference radiation outputs 3065 as input to coherence processor 3070. As will be described in further detail below, coherence processor 3070 is comprised of one or more coherence processors. Next, output from coherence processor 3070 is applied as input to analysis/display apparatus 3080. Embodiments of inspection applicator apparatus 3020, inspection collection apparatus 3020, reference collection and delay apparatus 3060, dispersal apparatus 3050, coherence processor 3070, and analysis/display apparatus 3080 will be described in detail below.

Figure 18:
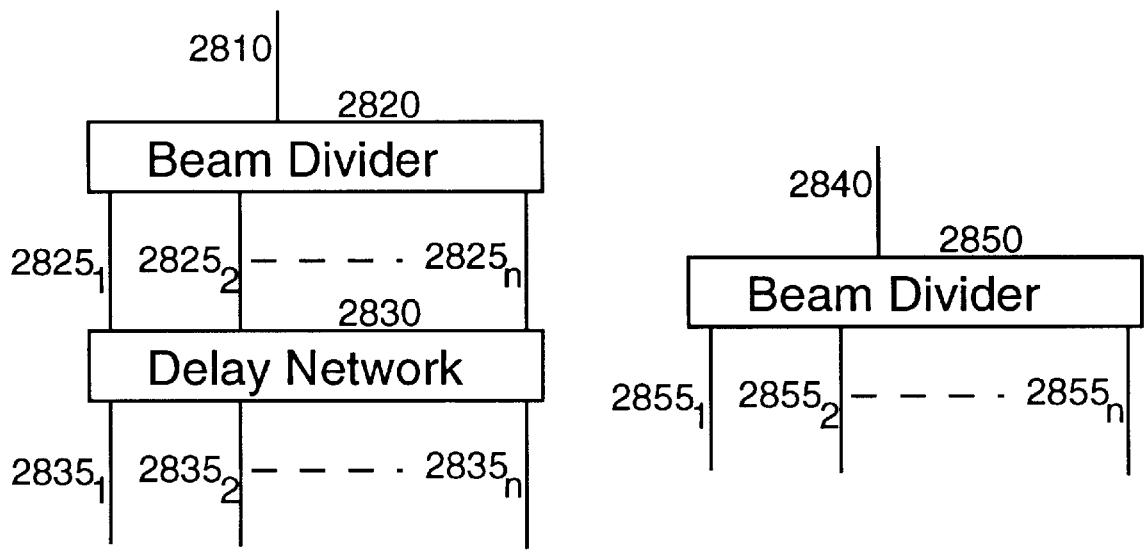
FIGS. 18–19 show block diagrams of dispersal apparatus that are used to fabricate embodiments of the second aspect of the present invention.

FIG. 18 shows, in pictorial form, a reference collection and delay apparatus and a dispersal apparatus for use in fabricating embodiments of the present invention, for example, embodiments shown in FIG. 2. As shown in FIG. 18, superbroad reference radiation from optical path 2810 is applied as input to beam divider 2820 and scattered inspection radiation output from optical path 2840 is applied as input to beam divider 2850. Beam divider 2820 divides the reference radiation applied as input from optical path 2810 into multiple beams and applies the multiple beams, in turn, as inputs to optical paths $2825_1$, $2825_2$, ..., $2825_n$. Reference radiation outputs from optical paths $2825_1$, $2825_2$, ..., $2825_n$ are applied as inputs to delay network 2830. Delay network 2830 delays the reference radiation inputs by predetermined amounts and applies the resulting delayed reference radiation outputs, in turn, as inputs to optical paths $2825_1$, $2825_2$, ..., $2825_n$, respectively. Finally, beam divider 2850 divides scattered inspection radiation applied as input from optical path 2840 into multiple beams and applies the multiple beams, in turn, as inputs to optical paths $2855_1$, $2855_2$, ..., $2855_n$. As can readily be appreciated by those of ordinary skill in the art, the predetermined delays introduced into the superbroad reference radiation enable an inspection apparatus fabricated in accordance with the embodiment shown in FIG. 2 to simultaneously provide spatial information from n different depths. As was discussed above, many ways of fabricating a delay network are known to those of ordinary skill in the art. For example, a delay network can be fabricated from an optical fiber network having paths which provide predetermined optical path differences among the inputs. Thus, whenever the term delay network is used herein, it is meant to be used in its most general and inclusive sense.

In accordance with the embodiment of the present invention shown in FIG. 2, the delayed reference radiation outputs from optical paths $2835_1$, $2835_2$, ..., $2835_n$ and the scattered inspection radiation outputs from optical paths $2855_1$, $2855_2$, ..., $2855_n$ are applied pairwise, respectively, as inputs to coherence processor 3070 of FIG. 2. In this embodiment, coherence processor 3070 is embodied as a multiplicity of coherence processors $3070_1$, $3070_2$, ..., $3070_n$.

Figure 19:
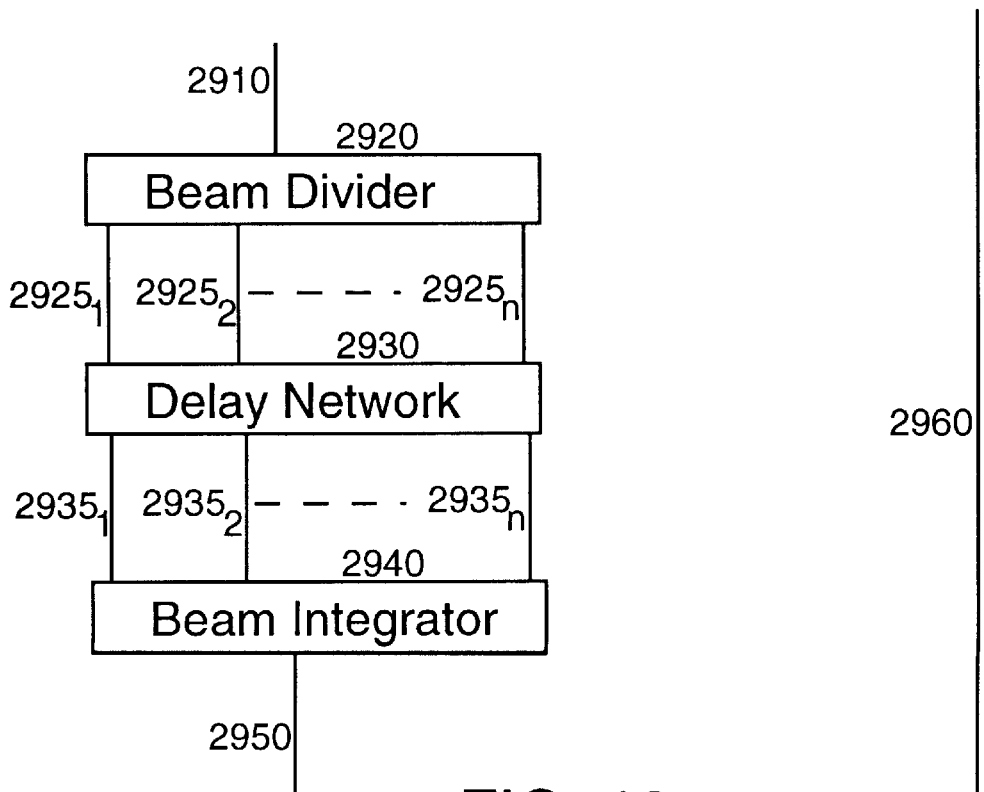

FIG. 19 shows, in pictorial form, a further embodiment of a reference collection and delay apparatus and a dispersal apparatus for use in fabricating embodiments of the present invention, for example, embodiments shown in FIG. 2. As shown in FIG. 19, superbroad reference radiation from optical path 2910 is applied as input to beam divider 2920 and scattered inspection radiation is output from optical path 2960. Beam divider 2920 divides the reference radiation applied as input from optical path 2910 into multiple beams and applies the multiple beams, in turn, as inputs to optical paths $2925_1$, $2925_2$, ..., $2925_n$. Reference radiation outputs from optical paths $2925_1$, $2925_2$, ..., $2925_n$ are applied as inputs to delay network 2930. Delay network 2930 delays the reference radiation inputs by predetermined amounts and applies the resulting delayed reference radiation outputs, in turn, as inputs to optical paths $2935_1$, $2935_2$, ..., $2935_n$, respectively. Finally, reference radiation outputs from optical paths $2935_1$, $2935_2$, ..., $2935_n$ are applied as inputs to beam integrator 2940. Beam integrator 2940 combines the radiation applied as inputs from optical paths $2935_1$, $2935_2$, ..., $2935_n$ into a single beam and applies the single beam of radiation, in turn, as input to optical path 2950.

In accordance with the embodiment of the present invention shown in FIG. 2, the delayed reference radiation output from optical path 2950 and the scattered inspection radiation output from optical path 2960 are applied as input to coherence 3070 of FIG. 2.

Figure 20:
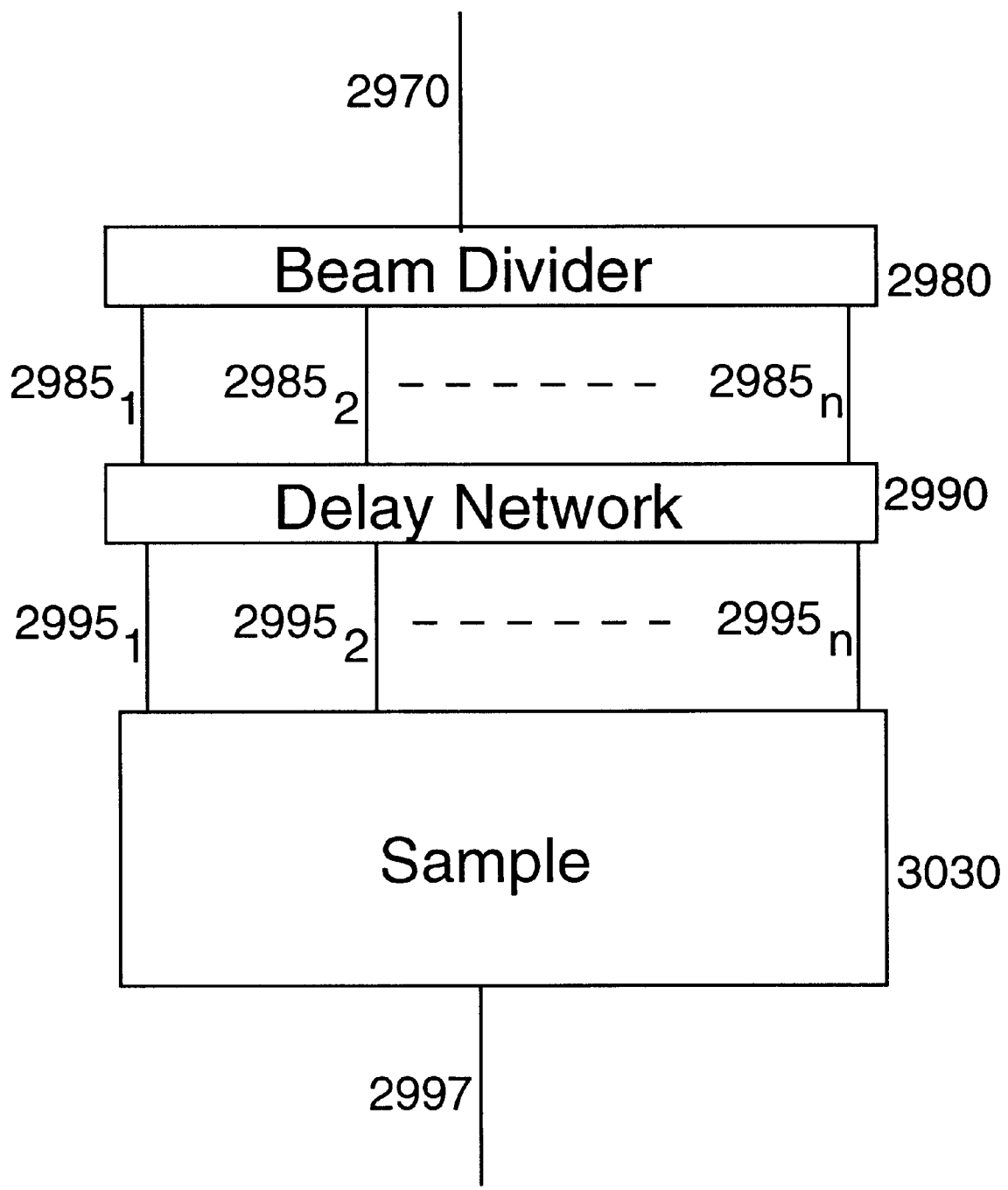
FIG. 20 shows a block diagram of an inspection applicator apparatus and an inspection collection apparatus that are used to fabricate embodiments of the second aspect of the present invention.

FIG. 20 shows, in pictorial form, an inspection applicator apparatus and an inspection collection apparatus for use in fabricating embodiments of the present invention such as, for example, embodiments shown in FIG. 2. As shown in FIG. 20, inspection radiation from optical path 2970 is applied as input to beam divider 2980. Beam divider 2980 divides the inspection radiation applied as input from optical path 2970 into multiple beams and applies the multiple beams, in turn, as inputs to optical paths $2985_1$, $2985_2$, ..., $2985_n$. Inspection radiation outputs from optical paths $2985_1$, $2985_2$, ..., $2985_n$ are applied as inputs to delay network 2990. Delay network 2990 delays the inspection radiation inputs by predetermined amounts and applies the resulting delayed inspection radiation outputs, in turn, as inputs to optical paths $2995_1$, $2995_2$, ..., $2995_n$, respectively. Next, the inspection radiation outputs from optical paths $2995_1$, $2995_2$, ..., $2995_n$ are applied as inputs to sample 3030. Next, inspection radiation that is scattered from sample 3030 is applied as input to optical path 2997. Finally, embodiments of the present invention as shown in FIG. 2 are fabricated using the embodiment of reference collection and delay apparatus 3060 shown in FIG. 19.

The following describes specific embodiments of the present invention in accordance with the embodiment of the second aspect of the present invention shown in FIG. 2.

Figure 21:
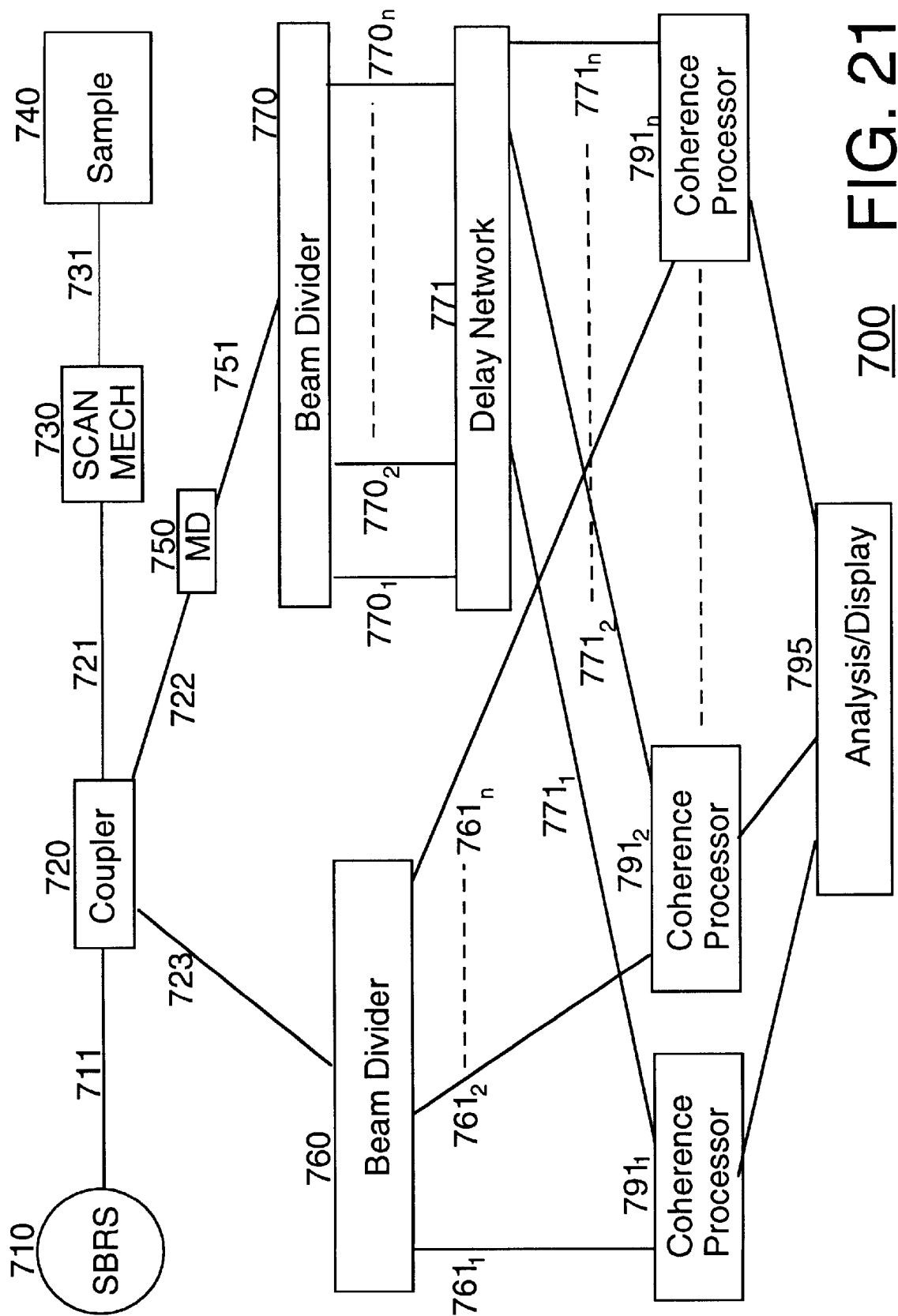
FIG. 21–23 show block diagrams of inspection apparatus that are fabricated in accordance with the second aspect of the present invention.

FIG. 21 shows a block diagram of inspection apparatus 700 that is fabricated in accordance with the second aspect of the present invention. As shown in FIG. 21, inspection apparatus 700 includes SBRS 710 which outputs superbroad radiation that is applied as input to optical path 711. The superbroad radiation output from optical path 711 is applied, in turn, as input to coupler 720. Next, coupler 720 applies a first portion of the input superbroad radiation as input to optical path 721 and applies a second portion of the input superbroad radiation as input to optical path 722. Next, the superbroad radiation output from optical path 721 is applied as superbroad inspection radiation input to scanning mechanism 730. Scanning mechanism 730 scans the superbroad inspection radiation applied as input from optical path 721 in a transverse direction, over optical path 731, across sample 740, for example a human eye. Inspection radiation that is backscattered from sample 740 is coupled as input to optical path 731. Next, the backscattered inspection radiation output from optical path 731 is applied as input to scanning mechanism 730, and scanning mechanism 730, in turn, applies the backscattered inspection radiation as input to optical path 721. Next, backscattered inspection radiation output from optical path 721 is applied as input to coupler 720, and coupler 720, in turn, applies the backscattered inspection radiation as input to optical path 723. Next, the backscattered inspection radiation output from optical path 723 is applied as input to beam divider 760. Although the embodiment of inspection apparatus 700 shown in FIG. 21 captures backscattered inspection radiation, the present invention is not so limited. As was explained in detail above, embodiments of the present invention can be used to capture inspection radiation that is scattered by the sample in any direction, including forward scattered inspection radiation.

The superbroad reference radiation output from optical path 722 is applied as input to optional frequency modulator MD 750. Next, reference radiation output from optional frequency modulator MD 750 is applied as input to optical path 751, and the reference radiation output from optical path 751 is applied, in turn, as input to beam divider 770. It should be understood by those of ordinary skill in the art that if MD 750 is not used, there is preferably a single optical path which transports the superbroad reference radiation from coupler 720 to beam divider 770.

Beam divider 760 and beam divider 770 divide the radiation outputs from optical paths 723 and 751, respectively, into multiple beams and apply the multiple beams, in turn, as inputs to optical paths $761_1$, $761_2$, ..., $761_n$ and optical paths $770_1$, $770_2$, ..., $7701_n$, respectively.

The useful number of multiple beams that beam divider 760 or beam divider 770 can provide depends on the intensity of the backscattered inspection radiation output from optical path 723 and the superbroad reference radiation output from optical path 751, respectively. The intensity of the backscattered inspection radiation output from optical path 723 is usually lower than the intensity of the reference radiation output from optical path 751. If necessary, in a particular embodiment, this difference in intensity can be overcome by appropriately amplifying the backscattered inspection radiation using optical amplifiers in any one of a number of places as was discussed above with respect to inspection apparatus 500 shown in FIG. 16.

As shown in FIG. 21, the reference radiation outputs from optical paths $770_1, 770_2, \ldots, 770_n$ are applied as inputs to delay network 771. Delay network 771 delays the reference radiation applied as input from optical paths $770_1, 770_2, \ldots, 770_n$ by predetermined amounts and applies the resulting delayed reference radiation outputs, in turn, as inputs to optical paths $771_1, 771_2, \ldots, 771_n$, respectively. As can readily be appreciated by those of ordinary skill in the art, the predetermined delays introduced into the superbroad reference radiation enable inspection apparatus 700 to simultaneously provide spatial information from n different depths.

As shown in FIG. 21, the backscattered inspection radiation outputs from optical paths $761_1, 761_2, \ldots, 761_n$ and the delayed reference radiation outputs from optical paths $771_1, 771_2, \ldots, 771_n$ are applied, pairwise respectively, as input to coherence processors $791_1, 791_2, \ldots, 791_n$, respectively. As was described above, coherence processors $791_1, 791_2, \ldots, 791_n$ utilize optical heterodyne techniques to measure coherent interference between the multiple beams output from optical paths $761_1, 761_2, \ldots, 761_n$ formed from the backscattered inspection radiation and the multiple beams output from optical paths $771_1, 771_2, \ldots, 771_n$ formed from the reference radiation. As is well known to those of ordinary skill in the art, to enhance the detection of the coherent interference output in the presence of the non-coherent output, a known beat signal is used. As was described above, such a beat signal can be introduced, for example, by an arrangement that varies the relative optical pathlength between the optical pathlength of the multiple beams output from optical paths $761_1, 761_2, \ldots, 761_n$ and the optical pathlength of the multiple beams output from optical paths $771_1, 771_2, \ldots, 771_n$. In FIG. 21 shows frequency modulator MD 750 located at one of the many positions it can be placed to provide the above-described function. As those of ordinary skill in the art will readily appreciation, MD 750 can also be placed in one or more of optical paths 721 and 723.

In a preferred embodiment of the present invention, coherence processors $791_1, 791_2, \ldots, 791_n$ are fabricated in accordance with the balanced heterodyne detection scheme described above in the Beaud article. However, in this embodiment, each of coherence processors $791_1, 791_2, \ldots, 791_n$ outputs a spatial structure of the sample for a depth corresponding to the particular, individual predetermined delay provided by delay network 771. Advantageously, in accordance with a preferred embodiment of the present invention, coherence processors $791_1, 791_2, \ldots, 791_n$ operate simultaneously to provide parallel processing so that n data points are collected simultaneously from n different spatial depths in sample 740 from one pulse output from SBRS 710.

As those of ordinary skill in the art will readily appreciate, in accordance with the present invention, the optical pathlengths for all the pairs of beams generated on one hand from backscattered inspection radiation from sample 740 and beams generated on the other hand from reference radiation output from coupler 720 and applied as input to optical path 722 and delayed by different amounts by delay network 771 to the respective coherence processors ought to be the same to within the coherence length of radiation output from SBRS 710. Finally, as shown in FIG. 21, the outputs from coherence processors $791_1, 791_2, \ldots, 791_n$ are transmitted to analysis/display module 797. Analysis/display module 797 displays spatial images of sample 740 from the n different spatial depths and also analyzes the structure of sample 740.

Figure 22:
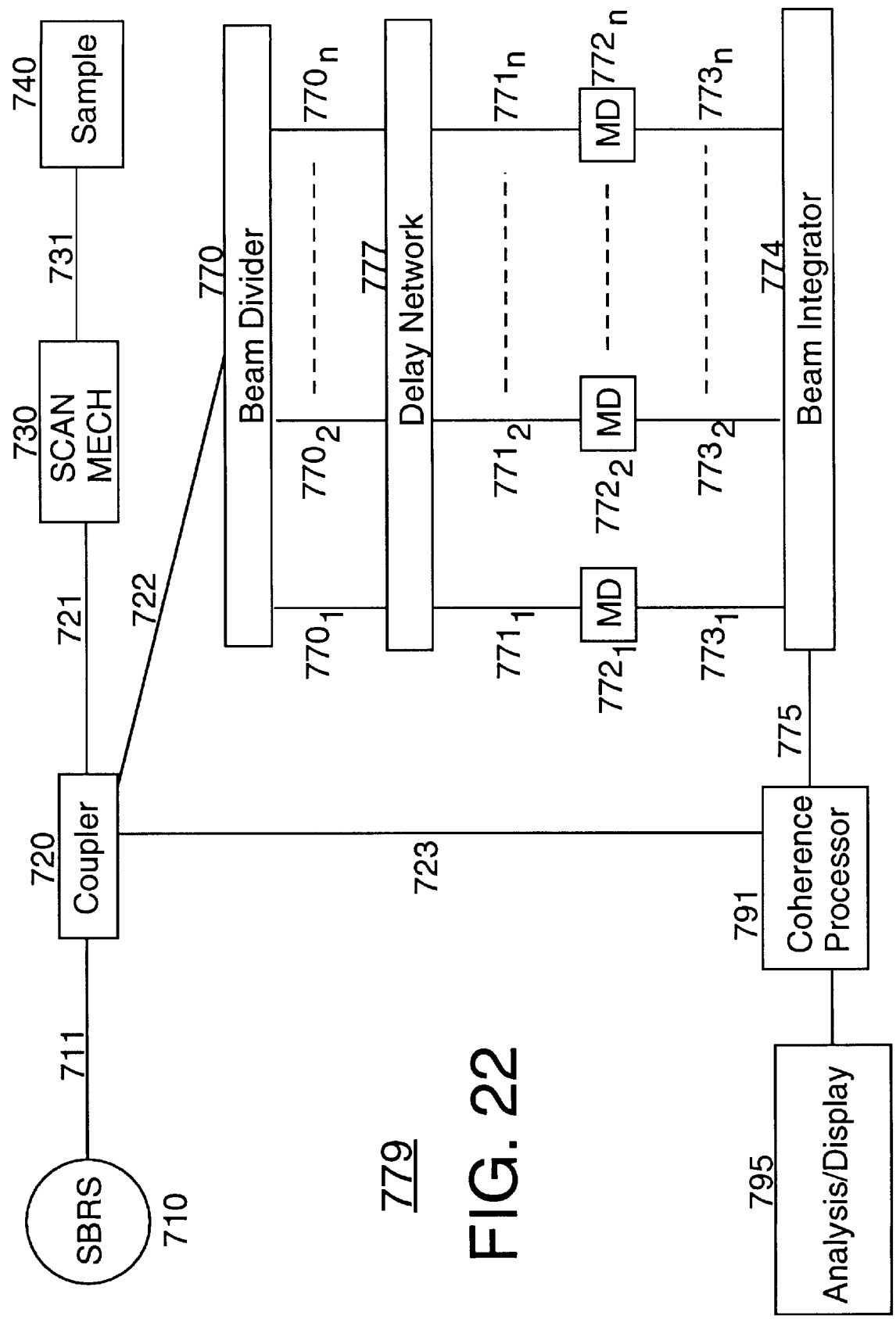

FIG. 22 shows a block diagram of inspection apparatus 779 which is an alternative embodiment of inspection apparatus 700 shown in FIG. 21. As shown in FIG. 22, inspection apparatus 700 includes SBRS 710 which outputs superbroad radiation that is applied as input to optical path 711. The superbroad radiation output from optical path 711 is applied as input to coupler 720. Next, coupler 720 applies a first portion of the input superbroad radiation as input to optical path 721 and applies a second portion of the input superbroad radiation as input to optical path 722. Next, the superbroad radiation output from optical path 721 is applied as superbroad inspection radiation input to scanning mechanism 730. Scanning mechanism 730 scans the superbroad inspection radiation applied as input from optical path 721 in a transverse direction, over optical path 731, across sample 740. Inspection radiation that is backscattered from sample 740 is applied as input to optical path 731. Next, the backscattered inspection radiation output from optical path 731 is applied as input to scanning mechanism 730, and scanning mechanism 730, in turn, applies the backscattered inspection radiation as input to optical path 721. Next, backscattered inspection radiation output from optical path 721 is applied as input to coupler 720, and coupler 720, in turn, applies the backscattered inspection radiation as input to optical path 723. Next, the backscattered inspection radiation output from optical path 723 is applied directly as input to coherence processor 791. Although the embodiment of inspection apparatus 779 shown in FIG. 22 captures backscattered inspection radiation, the present invention is not so limited. As was explained in detail above, embodiments of the present invention can be used to capture inspection radiation that is scattered by the sample in any direction, including forward scattered inspection radiation.

As shown in FIG. 22, superbroad reference radiation output from optical path 722 is applied as input to beam divider 770. Beam divider 770 divides the reference radiation output from optical path 722 into multiple beams and applies the multiple beams, in turn, as inputs to optical paths $770_1, 770_2, \ldots, 770_n$. The reference radiation outputs from optical paths $770_1, 770_2, \ldots, 770_n$ are applied as inputs to delay network 777. Delay network 777 delays the reference radiation applied as inputs from optical paths $770_1, 770_2, \ldots, 770_n$ by predetermined amounts and applies the resulting delayed reference radiation outputs, in turn, as inputs to optical paths $771_1, 771_2, \ldots, 771_n$, respectively. As can readily be appreciated by those of ordinary skill in the art, the predetermined delays introduced into the superbroad reference radiation enable inspection apparatus 779 to simultaneously provide spatial information from n different depths. The reference radiation outputs from optical paths $771_1, 771_2, \ldots, 771_n$ are applied as inputs to optional frequency modulators MD $772_1, 772_2, \ldots, 772_n$, respectively. The outputs from MD $772_1, 772_2, \ldots, 772_n$ are applied as inputs to optical paths $773_1, 773_2, \ldots, 773_n$, respectively, and the outputs from optical paths $773_1$, $773_2$, ..., $773_n$ are applied, in turn, as inputs to beam integrator 774. Beam integrator 774 combines the radiation inputs from optical paths $773_1$, $773_2$, ..., $773_n$ into a single beam and applies the single beam, in turn, as input to optical path 775. Next the optical radiation outputs from optical paths 723 and 775 are applied as inputs to coherence processor 791.

As was described above, coherence processor 791 utilizes optical heterodyne techniques to measure coherent interference between the reference radiation applied as input from optical path 775 and the backscattered inspection radiation applied as input from optical path 723. As is well known to those of ordinary skill in the art, to enhance the detection of the coherent interference output in the presence of the noncoherent output, known beat signals are used. As was described above, such a beat signal can be introduced, for example, by an arrangement that varies the relative optical pathlength between the optical pathlength of the radiation output from optical path 723 and the optical pathlength of the multiple beams output from optical path $771_1$, $771_2$, ..., $771_n$. Frequency modulators MD $772_1$, $772_2$, ..., $772_n$ shown in FIG. 22 provide the above described function of providing a beat signal. Frequency modulators MD $772_1$, $772_2$, ..., $772_n$ may be independent or may be linked together through harmonic mixing.

In a preferred embodiment of the present invention, coherence processor 791 is fabricated in accordance with the balanced heterodyne detection scheme described above in the Beaud article. However, in this embodiment, coherence processor 791 outputs a spatial structure of the sample for n depths corresponding to the n individual predetermined delays provided by delay network 777. Next, as shown in FIG. 22, the output from coherence processor 791 is applied as input to analysis/display module 797. Analysis/display module 797 displays spatial images of sample 740 from the n different spatial depths and also analyzes the structure of sample 740.

Figure 23:
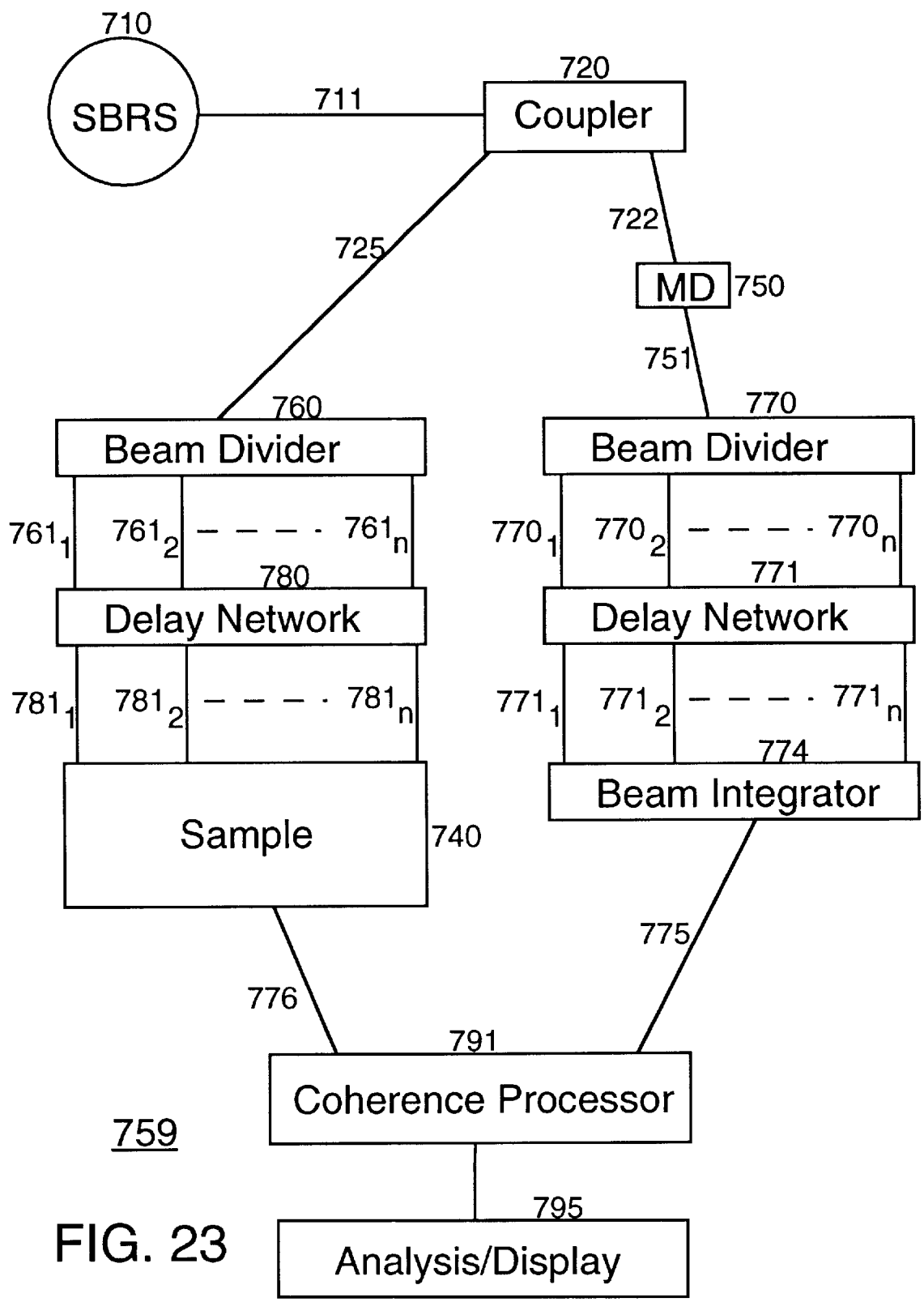

FIG. 23 shows a block diagram of inspection apparatus 759 which is an alternative embodiment of inspection apparatus 700 shown in FIG. 21. As shown in FIG. 23, inspection apparatus 700 includes SBRS 710 which outputs superbroad radiation that is applied as input to optical path 711. The superbroad radiation output from optical path 711 is applied as input to coupler 720. Next, coupler 720 applies a first portion of the input superbroad radiation as input to optical path 725 and applies a second portion of the input superbroad radiation as input to optical path 722.

The superbroad radiation output from optical path 725 is applied as superbroad inspection radiation input to beam divider 760. Beam divider 760 divides the superbroad inspection radiation applied as input from optical path 725 into multiple beams and applies the multiple beams, in turn, as inputs to optical paths $761_1$, $761_2$, ..., $761_n$. Next, the inspection radiation outputs from optical paths $761_1$, $761_2$, ..., $761_n$ are applied as inputs to delay network 780. Delay network 780 delays the inspection radiation applied as inputs from optical paths $761_1$, $761_2$, ..., $761_n$ by predetermined amounts and applies the resulting delayed inspection radiation outputs, in turn, as inputs to optical paths $781_1$, $781_2$, ..., $781_n$, respectively. As can readily be appreciated by those of ordinary skill in the art, the predetermined delays enable inspection apparatus 759 to simultaneously provide spatial information from n different depths and directions of beam incidence on sample 740. Next, the superbroad inspection radiation outputs from optical paths $781_1$, $781_2$, ..., $781_n$ are applied as inputs to sample 740. Next, inspection radiation scattered by sample 740 is applied as input to optical path 776. As can readily be appreciated, the scattered radiation can be collected from n different scattering angles, such as, backward scattering, forward scattering and so forth. In addition, the scattered radiation can be collected from n different transverse positions, including positions at the same depth, by appropriately setting the predetermined delays. Further, the sample can be moved to enable the apparatus to probe different spatial points and different angles or different depths at different transverse positions.

The reference radiation output from optical path 722 is applied as input to optional frequency modulator MD 750. Reference radiation output from optional frequency modulator MD 750 is applied as input to optical path 751 and the reference radiation output from optical path 751 is applied, in turn, as input to beam divider 770. It should be understood by those of ordinary skill in the art that if MD 750 is not used, there is preferably a single optical path which transports the reference radiation from coupler 720 to beam divider 770. Beam divider 770 divides the reference radiation output from optical path 751 into multiple beams and applies the multiple beams, in turn, as inputs to optical paths $770_1$, $770_2$, ..., $770_n$. Next, the reference radiation outputs from optical paths $770_1$, $770_2$, ..., $770_n$ are applied as inputs to delay network 771. Delay network 771 delays the reference radiation applied as inputs from optical paths $770_1$, $770_2$, ..., $770_n$ by predetermined amounts and applies the resulting delayed reference radiation outputs, in turn, as inputs to optical paths $771_1$, $771_2$, ..., $771_n$, respectively. Next, the reference radiation outputs from optical paths $771_1$, $771_2$, ..., $771_n$ are applied as inputs to beam integrator 774. Beam integrator 774 combines the reference radiation applied as inputs from optical paths $771_1$, $771_2$, ..., $771_n$ into a single beam and applies the single beam, in turn, as input to optical path 775. Next the radiation outputs from optical paths 775 and 776 are applied as inputs to coherence processor 791.

As was described above, coherence processor 791 utilizes optical heterodyne techniques to measure coherent interference between scattered inspection radiation output from optical path 776 and reference radiation output from optical path 775. As is known to those of ordinary skill in the art, to enhance detection of the coherent interference output in the presence of non-coherent output, a known beat signal is used. As was described above, such a beat signal can be introduced, for example, by an apparatus that varies the relative optical pathlength difference between the optical pathlength traveled by the multiple beams output from optical paths $761_1$, $761_2$, ..., $761_n$ and the optical pathlength traveled by the multiple beams output from optical paths $770_1$, $770_2$, ..., $770_n$. FIG. 23 shows frequency modulator MD 750 located at one of the many positions it can be positioned to provide the above-described function. As those of ordinary skill in the art will readily appreciation, MD 750 can also be placed in one or more of the optical paths to provide this function.

In a preferred embodiment of the present invention, coherence processor 791 is fabricated in accordance with the balanced heterodyne detection scheme described above in the Beaud article. However, in this embodiment, coherence processor 791 outputs a spatial structure of the sample for, for example, n depths corresponding to the n individual predetermined delays provided by delay networks 771 and 780. Advantageously, in accordance with a preferred embodiment of the present invention, coherence processor 791 operates to provide parallel processing so that n data points are collected simultaneously from n different spatial depths in sample 740 from one pulse output from SBRS 710.

As those of ordinary skill in the art will readily appreciate, in accordance with the present invention, the optical pathlengths for all the pairs of beams generated on one hand from inspection radiation scattered from sample 740 and beams generated on the other hand from reference radiation output from coupler 720 and applied as input to optical path 722 and delayed by different amounts by delay network 771 to the coherence processor ought to be the same to within the coherence length of the radiation output from SBRS 710. Finally, as shown in FIG. 23, the output from coherence processor 791 is applied as input to analysis/display module 797. Analysis/display module 797 displays spatial images of sample 740 from the n different spatial depths, n different angles, and so forth as described above and also analyzes the structure of sample 740.

The following is a description of an embodiment of a third aspect of the present invention, which description provides a broad overview of the third aspect of the present invention as it pertains to inspection of wafers, masks such as photomasks, and the like used in the semiconductor industry to fabricate circuits, memory, and the like.

Figure 3:
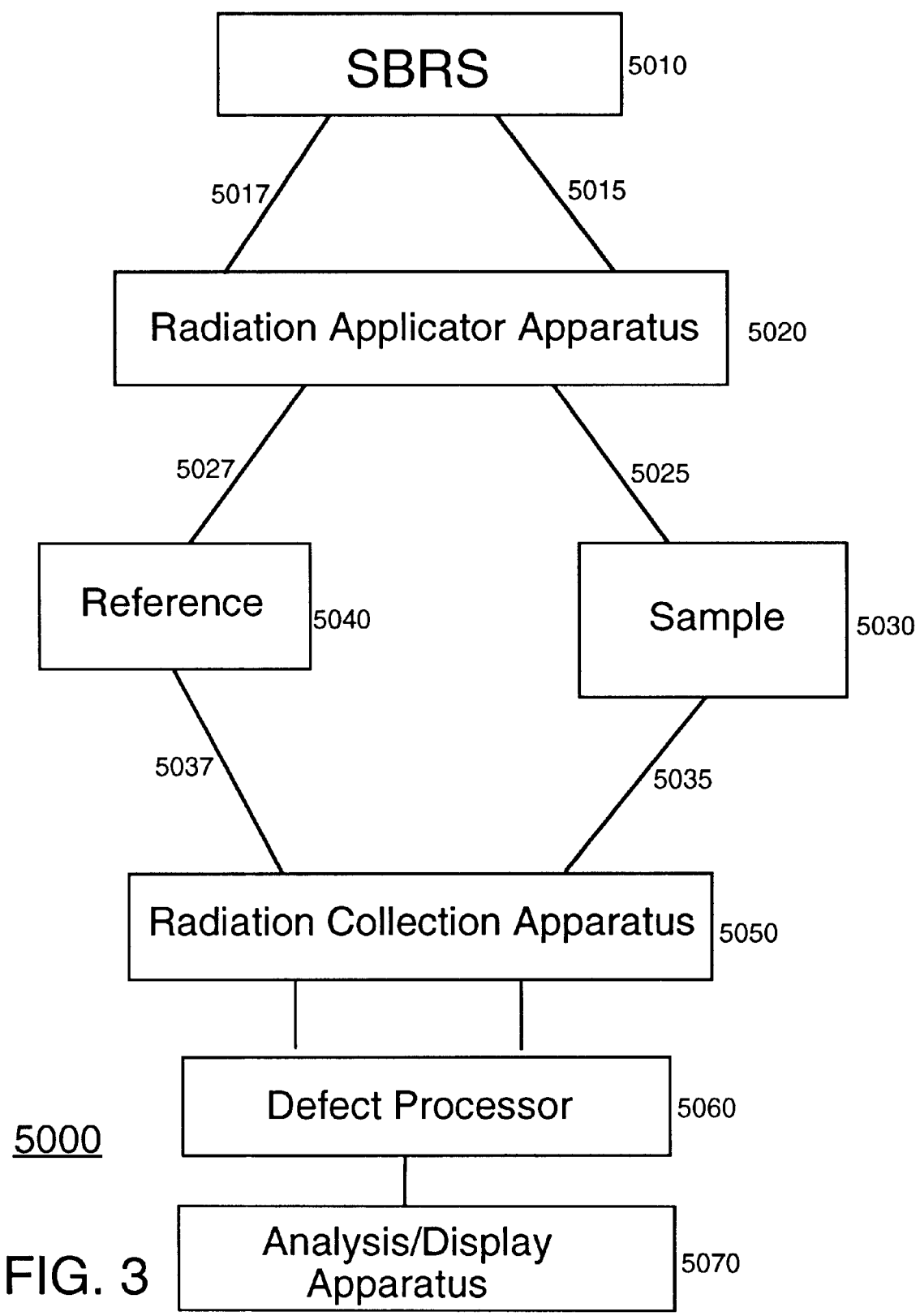
FIG. 3 shows a block diagram of an inspection apparatus that is fabricated in accordance with a third aspect of the present invention.

FIG. 3 shows a block diagram of inspection apparatus 5000 that is fabricated in accordance with the third aspect of the present invention. As shown in FIG. 3, inspection apparatus 5000 includes superbroad radiation source 5010 ("SBRS 5010") which outputs superbroad inspection radiation 5015 and superbroad reference radiation 5017. Inspection radiation 5015 and reference radiation 5017 are applied as input to radiation applicator apparatus 5020. Next, radiation applicator apparatus 5020 applies inspection radiation 5025 as input to sample 5030 and radiation applicator 5020 applies reference radiation 5027 as input to reference 5040. Next, radiation collection apparatus 5050 collects at least a portion of the inspection radiation that is scattered by sample 5030 (scattered inspection radiation 5035) and at least a portion of the reference radiation that is scattered by reference 5040 (scattered reference radiation 5037). Next, radiation collection apparatus 5050 applies the scattered inspection radiation and the scattered reference radiation as input to defect processor 5060. Finally, an output from defect processor 5060 is applied as input to analysis/display apparatus 5070. Embodiments of radiation applicator apparatus 5020, reference 5040, radiation collection apparatus 5050, defect processor 5060, and analysis/display apparatus 5070 will be described in detail below in connection with specific embodiments of the present invention.

The following describes specific embodiments of the present invention in accordance with the embodiment of the third aspect of the present invention shown in FIG. 3.

Figure 24:
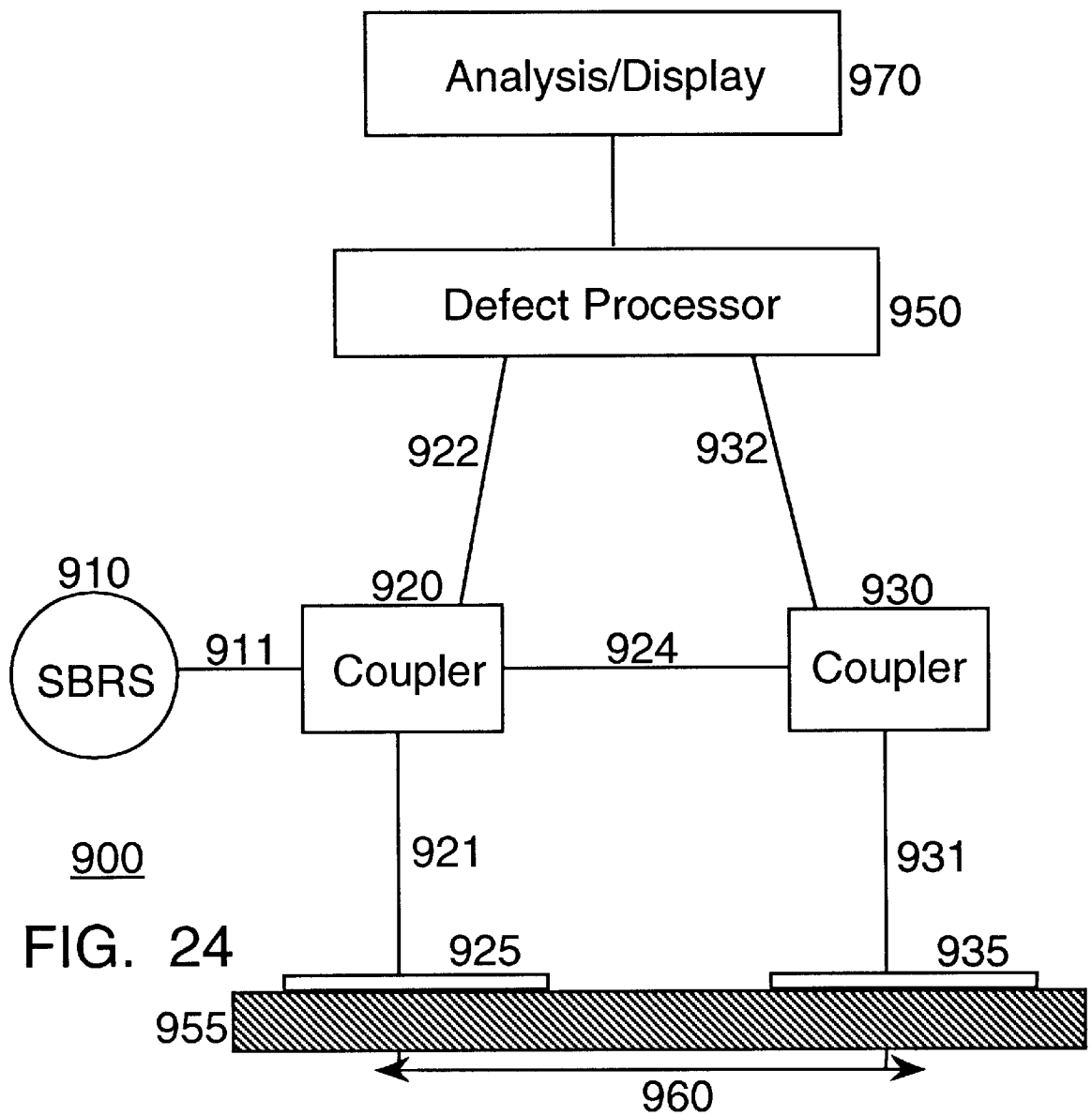

FIG. 24 shows a block diagram of inspection apparatus 900 which is fabricated in accordance with the present invention for use, for example, in inspecting wafers, photomasks, and the like used in the semiconductor industry to fabricate circuits, memory, and the like. As shown in FIG. 24, superbroad radiation output from SBRS 910 is applied as input to optical path 911, and optical path 911, in turn, applies the superbroad radiation output from optical path 911 as input to coupler 920. Coupler 920 applies a first portion of the incident superbroad radiation as input to optical path 921 as reference radiation, and coupler 920 applies a second portion of the incident superbroad radiation as input to optical path 924 as inspection radiation. Next, superbroad reference radiation output from optical path 921 impinges upon standard 925 which is disposed on table 955. As shown in FIG. 24, and as will be explained in detail below, standard 925 acts as a reference and can be embodied as a wafer, photomask, and the like.

Superbroad inspection radiation output from optical path 924 is applied as input to coupler 930, and coupler 930, in turn, applies at least a portion of the radiation applied as input from optical path 924 as input to optical path 931. Next, superbroad inspection radiation output from optical path 931 impinges upon sample 935 which is disposed on table 955. In accordance with the present invention, sample 935 may be a wafer, a photomask, and the like which are used in the semiconductor industry to fabricate circuits, memory, and the like. Those of ordinary skill in the art should readily appreciate that the radiation applied to standard 925 and to sample 935 may be transmitted thereto in a number of alternative ways which are understood to also be within the scope of the present invention. For example, the superbroad radiation output from SBRS 910 can be split and each of the resultant radiation outputs can be applied separately to couplers 920 and 930.

Table 955 is fabricated in accordance with any number of ways which are well known to those of ordinary skill in the art to be substantially flat and to have apparatus (not shown) for translating the table along at least the direction shown by arrow 960 and for holding the reference and sample substantially flat on table 955. Further, the superbroad radiation applied to standard 925 and to sample 935 can be scanned in a direction transverse to the direction shown by arrow 960 by apparatus (not shown) which are well known to those of ordinary skill in the art. This enables an area (typically the whole area) of sample 935 to be analyzed. Although, in most case, samples to be examined are substantially flat wafers, the present invention is not thereby limited. In cases where the sample is not flat and has some curvature, for example, a surface of a lens, the table may similarly be not flat, or the table may configured in a manner which is well known to those of ordinary skill in the art to move along a particular direction of the surface. Thus, whenever the term table is used herein, it is meant to be used in its most general and inclusive sense.

Reference radiation scattered from standard 925 is applied as input to optical path 921, and scattered reference radiation output from optical path 921 is applied, in turn, as input to coupler 920. Next, coupler 920 applies at least a portion of the scattered reference radiation as input to optical path 922. Next, scattered reference radiation output from optical path 922 is applied as input to coherence processor 950. Inspection radiation scattered from sample 935 is applied as input to optical path 931, and scattered inspection radiation output from optical path 931 is applied, in turn, as input to coupler 930. Next, coupler 930 applies at least a portion of the scattered inspection radiation as input to optical path 932. Next, scattered inspection radiation output from optical path 932 is applied as input to defect processor 950.

Finally, the output from defect processor 950 is applied as input to analysis/display module 970. Defect processor 950 and analysis/display module 970 may operate in the same manner described above for the coherence processor and the analysis/display module of preceding embodiments to provide a spatial image of the sample or they may operate to identify defects on or in a sample by investigating differences between radiation scattered from (diffracted by) the reference and radiation scattered from (diffracted by ) the sample. The differences can be measured directly by analyzing coherent interference between the two radiation signals or the differences can be measured indirectly by analyzing correlations between the two radiation signals. In this latter mode, defect processor 950 produces the coherent interference and/or the correlation and analysis/display module 970 analyzes the results produced thereby.

Coherent interference measurement methods and correlation measurement methods are particularly suitable for comparing two portions within a wafer, a photomask, and the like which are used in the semiconductor industry to fabricate circuits, memory and the like. In carrying out such a comparison, one portion of the wafer is taken as a reference and another portion of the wafer is taken as a sample to be inspected. Defect processor 950 and analysis/display module 970 will reveal whether the radiation scattered from (diffracted by) both portions of the wafer are the same or not. In accordance with the present invention, the existence of measurable differences indicates that the portions being compared are not the same and that one of them has defects.

Coherent interference measurement methods and correlation measurement methods are well known to those of ordinary skill in the art. As such the following discussion is not meant to be limiting, but merely illustrative. Measurements of coherent interference, in essence, are used to analyze phase differences between radiation scattered from the reference and the sample. Defects on or in the sample will produce phase differences (typically, as a function of radiation frequency) between radiation scattered from the sample and radiation scattered from the reference. If there were no defect, one would expect there to be no phase differences between the scattered radiation signals. Thus, if there were no defect and one were to cause the radiation signals to destructively interfere (by, for example, changing the phase of the radiation scattered from the reference by 180°), one would expect to see complete destructive interference. However, if there were a defect, its presence can be detected by causing the radiation signals to interfere and by analyzing the lack of complete destructive interference, i.e., the presence of phase differences in radiation scattered from the reference and the sample indicates the existence of defects. Further, it is expected that different types of defects will cause different types of phase variations (also as a function of frequency) and that characteristic signatures may be developed by those of ordinary skill in the art to identify different types of defects. Such analysis will be done by analysis/display module 970. In one embodiment, this will be done by comparing outputs received from defect processor 950 with libraries (for example, stored libraries) of characteristic patterns or data. In other embodiments, this can be done in coordination with operator input. Since superbroad inspection radiation allows one to examine a small spatial region of the sample using coherent measurements, inspection apparatus 900 is very sensitive in identifying defects.

Correlation methods usually investigate variational dependencies on relative optical pathlength differences between radiation scattered from the reference and the sample, respectively. One simple correlation method is an amplitude correlation. In this case, when the sample to be inspected has no defects, the amplitude correlation between the signal scattered from reference and the sample is a maximum at zero relative optical pathlength difference. On the other hand, when the sample is contaminated with a defect, this is no longer true. Thus, changes in correlation characteristics are analyzed by analysis/defect processor 970 to indicate the presence of a defect.

Multiplicities of collectors (for example, collectors for different scattering directions) may be used to obtain detection of differences for different scattering directions. The comparisons of differences between radiation scattered from the reference and the sample at a multiplicity of different directions can be used to eliminate false detection of defects. The comparisons can be performed using standard analysis algorithms for, for example, pattern recognition. Also, specific algorithms may be developed for analysis of application-specific cases. For example, algorithms and collector combinations can be optimized to detect defects produced by particular mechanisms in semiconductor fabrication. One instance of this would be an arrangement of algorithms and collectors to detect scratches on metal layers produced by chemical mechanical polishing processes.

Although FIG. 24 shows standard 925 and sample 935 to be separate objects, in accordance with the present invention, standard 925 and sample 935 may be different portions of the same object such as, for example, different portions of a single wafer. Further, although FIG. 24 shows an embodiment where radiation is backscattered from standard 925 and sample 935, the present invention is not limited to this embodiment. As will be described in detail below, embodiments of the present invention can be used to collect radiation scattered from angles other than 180° and, in fact, radiation that is scattered in a multiplicity of directions at the same time can be used. Still further, the present invention is not limited to embodiments where the standard and the sample are disposed in the same plane.

Figure 25:
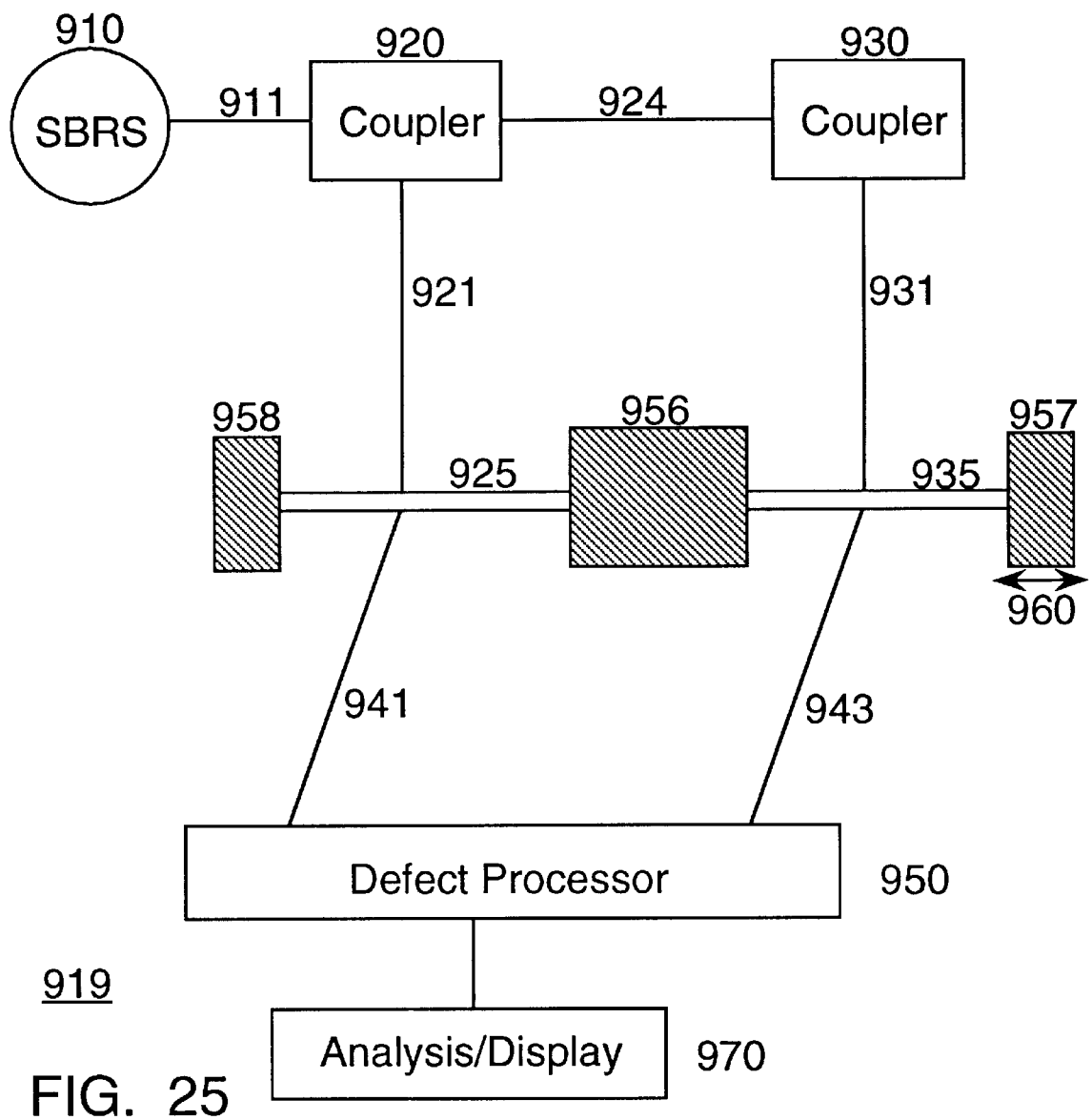

FIG. 25 shows a block diagram of inspection apparatus 919 which is an alternative embodiment of inspection apparatus 900 shown in FIG. 24. As shown in FIG. 25, superbroad radiation output from SBRS 910 is applied as input to optical path 911, and optical path 911, in turn, applies the superbroad radiation output from optical path 911 as input to coupler 920. Coupler 920 applies a first portion of the incident superbroad radiation as input to optical path 921 as reference radiation and a second portion of the incident superbroad radiation as input to optical path 924 as inspection radiation. Next, superbroad reference radiation output from optical path 921 impinges upon standard 925 which is disposed within holding apparatus 956 and 958 of a table (not shown), where holding apparatus 956 and 958 are affixed to, and move with, the table. There are many ways known to those of ordinary skill in the art for fabricating such holding apparatus. Thus, whenever the term holding apparatus is used herein, it is meant to be used in its most general and inclusive sense. As shown in FIG. 25, and as will be explained in detail below, standard 925 acts as a reference and can be embodied as a wafer, photomask, and the like.

Superbroad inspection radiation output from optical path 924 is applied as input to coupler 930, and coupler 930, in turn, applies at least a portion of the radiation applied as input from optical path 924 to optical path 931. Next, superbroad inspection radiation output from optical path 931 impinges upon sample 935 which is disposed within holding apparatus 956 and 957, where holding apparatus 956 and 957 are affixed to and move with the table. In accordance with the present invention, sample 935 may be a wafer, a photomask, and the like which are used in the semiconductor industry to fabricate circuits, memory, and the like. Those of ordinary skill in the art should readily appreciate that the radiation applied to standard 925 and to sample 935 may be transmitted thereto in a number of alternative ways which are understood to also be within the scope of the present invention. For example, the superbroad radiation output from SBRS 910 can be split and each resultant beam of radiation can be applied separately to couplers 920 and 930.

The table includes apparatus (not shown) for translating the table along at least the direction shown by arrow 960. Further, the superbroad radiation applied to standard 925 and to sample 935 can be scanned in a direction transverse to the direction shown by arrow 960 by apparatus (not shown) which are well known to those of ordinary skill in the art. This enables an area (typically the whole area) of sample 935 to be analyzed. Although, in most case, samples to be examined are substantially flat wafers, the present invention is not thereby limited. In cases where the sample is not flat and has some curvature, for example, a surface of a lens, the table may similarly be not flat, or the table may configured in a manner which is well known to those of ordinary skill in the art to move along a particular direction of the surface.

Reference radiation scattered from standard 925 is applied as input to optical path 941, and scattered reference radiation output from optical path 941 is applied, in turn, as input to defect processor 950. Inspection radiation scattered from sample 935 is applied as input to optical path 943, and scattered inspection optical radiation output from optical path 943 is applied, in turn, as input to defect processor 950. Finally, the output from defect processor 950 is applied as input to analysis/display module 970. Defect processor 950 and analysis/display module 970 operate in the same manner as described above to provide a spatial image of the surface of sample 935 and/or to investigate differences between signals scattered from (diffracted by) the reference and the sample.

Thus, inspection apparatus 919 shown in FIG. 25 is used to provide images and/or to investigate differences using forward scattered low coherence radiation. Although FIG. 25 shows standard 925 and sample 935 to be separate objects, in accordance with the present invention, standard 925 and sample may be different portions of the same object such as, for example, different portions of a single wafer.

It is noted that embodiments of the present invention may be comprised of combinations of the embodiments shown in FIGS. 24 and 25 where scattered radiation may be detected from a number of different backscattered angles and from a number of different forward scattered angles at the same time. Further, embodiments of the present invention can be utilized to utilize one standard and to obtain images from a multiplicity of positions on the sample at the same time using output from one superbroad radiation or using many superbroad radiation sources having the same and/or different frequency spectra output ranges.

Figure 26:
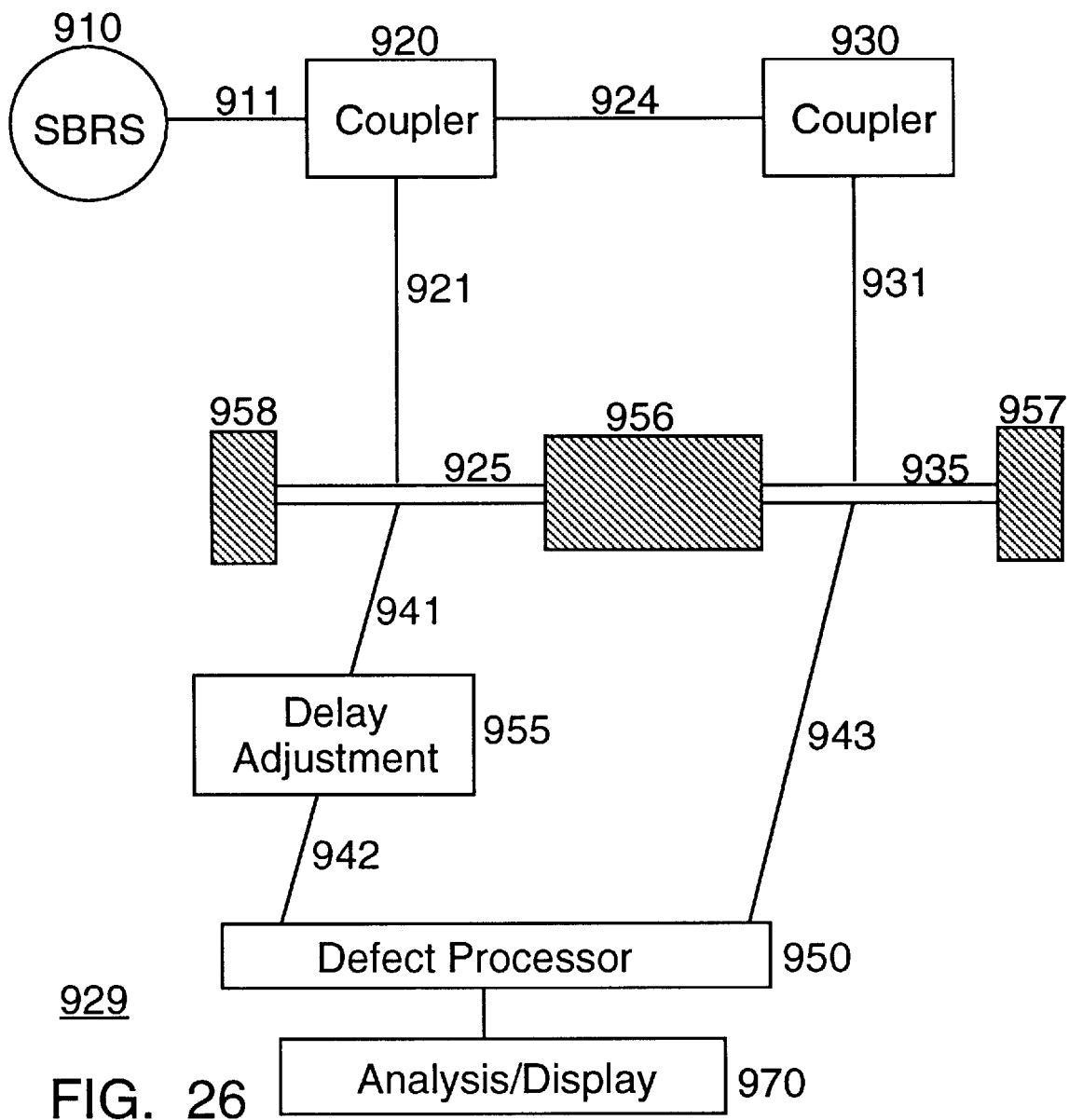

FIG. 26 shows a block diagram of inspection apparatus 929 which is an alternative embodiment of inspection apparatus 919 shown in FIG. 25. The description of inspection apparatus 929 is the same as that given above for inspection apparatus 919 except for the following difference. As shown in FIG. 26, delay adjustment apparatus 955 is disposed in the optical path between standard 925 and defect processor 950. Delay adjustment apparatus 955 alters the optical pathlength of radiation applied as input to defect processor 950. Many ways of making a delay adjustment apparatus are known to those of ordinary skill in the art. Thus, whenever the term delay adjustment apparatus is used herein, it is meant to be used in its most general and inclusive sense.

In accordance with the present invention, changes in optical pathlength produced by delay adjustment apparatus 955 enable inspection apparatus 929 to provide spatial depth measurements for sample 935. It is noted, that further embodiments of the present invention comprise combinations of the embodiments shown in FIGS. 24–26.

In accordance with present invention, in order to increase the speed of inspection, methods and apparatus are fabricated to concurrently image an area on the sample to provide parallel processing. This is accomplished by imaging the superbroad radiation in the above described embodiments of FIGS. 24–26 in, for example, a fan shaped beam or a cone shaped beam. Many ways of providing such a fan shaped beam or cone shaped beam are known to those of ordinary skill in the art.

In a preferred embodiment, the fan shaped beam or cone shaped beam is oriented so that it impinges upon the surfaces of standard 925 and sample 935 at an angle. In accordance with the present invention, this will create different time delays for radiation scattered from various parts of the area, i.e., the impingement area of the fan shaped beam or cone shaped beam on the standard 925 and the sample 935. For embodiments where the scattered radiation used is scattered in backward directions, the scattered radiation from various parts of the area are simultaneously collected for parallel processing in accordance with methods that have been described in detail above. In preferred embodiments, the direction in which the superbroad radiation beam is spread is substantially perpendicular to the motion of the table. Thus, as the table moves, strips of the sample will be analyzed.

As was described above, beam dividers, spectrum separators, delay networks, beam integrators, beam modulators and so forth are basic components of embodiments of the present invention. It should be understood that such devices can be fabricated in a number of ways and that they may even be integrated to form simpler devices. Such integrated devices can take many different forms. For example, an integrated beam divider, delay network and a beam integrator may be comprised of an optical fiber with several notches or a device with several semi-transparent mirrors as well as a device comprised of a fan-beam launcher, a grating-like reflector, and a fan-beam receptor.

In accordance with the present invention, the use of a variable optical delay line may be used to replace, or may be used in conjunction with, a mechanical mechanism for varying the relative optical pathlength difference between the optical paths traveled by the inspection radiation and the optical paths traveled by the reference radiation. The use of the variable optical delay line is advantageous because it eliminates the problems associated with prior art mechanical apparatus. Further, it should be clear to those of ordinary skill in the art that such variable optical delay lines may be placed in the path of the reference radiation or it may be placed in the path of the inspection radiation, or both, to vary the relative optical pathlength difference therebetween and, thereby, to provide a mechanism for further scanning samples in depth.

In some embodiments of the present invention, it is possible to accelerate the speed of inspection by deploying a front end apparatus to screen a sample, to select an area of interest for subsequent high precision examination, to align and to determine the approximate pathlength induced by the selected area, and to monitor environmental disturbance on the sample. A preferred front end operates online swiftly to provide timely information without delays.

The front end apparatus is an apparatus having less precision and sophistication than the high speed, high precision apparatus described above. For example, continuous radiation, without the restriction of a window, can be used to screen the sample and to select the area of interest. Pulsed radiation, with the help of coherence processors can be used to perform other front end functions. It is advantageous to select radiation for use in the front end apparatus that has different frequencies that that of the superbroad radiation used to fabricate embodiments of the present invention described above. The difference will ease the coupling and decoupling of the radiation from interfering with the high precision measurements. Font ends may have different variations. A person with ordinary skill in the art, with the help of the present teaching, should be able to construct various front end apparatus.

Those skilled in the art will recognize that the foregoing description has been presented for the sake of illustration and description only. As such, it is not intended to be exhaustive or to limit the invention to the precise form disclosed.

What is claimed is:

1. An inspection apparatus for inspecting a sample which comprises:

a source of superbroad inspection radiation having a frequency spectrum with an inspection width and reference radiation;

an inspection applicator apparatus which applies the inspection radiation as input to the sample;

an inspection collector apparatus which collects at least a portion of the inspection radiation that is scattered by the sample and applies at least a portion of the scattered inspection radiation as input to a dispersal apparatus;

wherein the dispersal apparatus applies radiation from the scattered inspection radiation as input to a plurality of coherence processors and applies radiation from the reference radiation as input to the plurality of coherence processors; and a processor that fourier analyzes outputs from the coherence processors.

2. The inspection apparatus of claim 1 wherein the dispersal apparatus applies the scattered inspection radiation and the reference radiation so that the width of the frequency spectrum of the radiation from the scattered inspection radiation that is applied as input to the coherence processors is substantially the same as the inspection width and the width of the frequency spectrum of the radiation from the reference radiation that is applied as input to the coherence processors is less than the inspection width.

3. The inspection apparatus of claim 1 wherein the dispersal apparatus applies the scattered inspection radiation and the reference radiation so that the width of the frequency spectrum of the radiation from the scattered inspection radiation that is applied as input to the coherence processors is less than the inspection width and the width of the frequency spectrum of the radiation from the reference radiation that is applied as input to the coherence processors substantially the same as the inspection width.

4. The inspection apparatus of claim 1 wherein the dispersal apparatus applies the scattered inspection radiation and the reference radiation so that the width of the frequency spectrum of the radiation from the scattered inspection radiation that is applied as input to the coherence processors is less than the inspection width and the width of the frequency spectrum of the radiation from the reference radiation that is applied as input to the coherence processors is less than the inspection width.

5. The inspection apparatus of claim 2 wherein the dispersal apparatus comprises a beam divider responsive to the scattered inspection radiation and a spectrum separator responsive to the reference radiation.

6. The inspection apparatus of claim 3 wherein the dispersal apparatus comprises a spectrum separator responsive to the scattered inspection radiation and a beam divider responsive to the reference radiation.

7. The inspection apparatus of claim 4 wherein the dispersal apparatus comprises a spectrum separator responsive to the scattered inspection radiation and a spectrum separator responsive to the reference radiation.

8. The inspection apparatus of claim 1 wherein the source of superbroad inspection radiation and superbroad reference radiation comprises a multiplicity of radiation sources whose outputs are each applied as input to a beam integrator to output the superbroad inspection radiation.

9. The inspection apparatus of claim 8 wherein the source further comprises one or more beam windows each of which is responsive to an output from one of the radiation sources, which one or more beam widow adjusts the frequency spectrum of the radiation input thereto and outputs radiation having a predetermined frequency spectrum and pulse width.

10. The inspection apparatus of claim 8 wherein radiation from the multiplicity of radiation sources are applied as inputs to the dispersal apparatus.

11. The inspection apparatus of claim 10 wherein the dispersal apparatus applies the scattered inspection radiation so that the width of the frequency spectrum of the radiation from the scattered inspection radiation that is applied as input to the coherence processors is substantially the same as the inspection width.

12. The inspection apparatus of claim 10 wherein the dispersal apparatus applies the scattered inspection radiation so that the width of the frequency spectrum of the radiation from the scattered inspection radiation that is applied as input to the coherence processors is less than the inspection width.

13. The inspection apparatus of claim 11 wherein the dispersal apparatus comprises a beam divider responsive to the scattered inspection radiation.

14. The inspection apparatus of claim 12 wherein the dispersal apparatus comprises a spectrum separator responsive to the scattered inspection radiation.

15. The inspection apparatus of claim 1 which further comprises a variable optical delay line disposed to variably delay the relative optical pathlength between the inspection radiation and the reference radiation.

16. An inspection apparatus for inspecting a sample which comprises:

a source of radiation which outputs: (a) superbroad inspection radiation having a frequency spectrum with an inspection width and (b) one or more reference radiation outputs, each of the one or more reference radiation outputs having a reference frequency spectrum with a reference width that is less than or substantially equal to the inspection width;

an inspection applicator apparatus which applies the inspection radiation as input to the sample;

an inspection collection apparatus which collects at least a portion of the inspection radiation that is scattered by the sample and applies at least a portion of the scattered inspection radiation as input to a dispersal apparatus;

a reference collection apparatus which applies radiation from the one or more reference radiation outputs as input to the dispersal apparatus;

wherein the dispersal apparatus applies radiation from the scattered inspection radiation as input to a plurality of coherence processors and applies radiation from the one or more reference radiation outputs to the plurality of coherence processors;

wherein the width of the frequency spectrum of the radiation from the scattered inspection radiation that is applied as input to the coherence processors and the width of the frequency spectrum of the radiation from the one or more reference radiation outputs that is applied as input to the coherence processors satisfy one of the following:

the width of the frequency spectrum of the radiation from the scattered inspection radiation is substantially the same as the inspection width and the width of the frequency spectrum of the radiation from the one or more reference radiation outputs is less than the inspection width; or the width of the frequency spectrum of the radiation from the scattered inspection radiation is less than the inspection width and the width of the frequency spectrum of the radiation from the one or more reference radiation outputs is substantially the same as the inspection width; or the width of the frequency spectrum of the radiation from the scattered inspection radiation is less than the inspection width and the width of the frequency spectrum of the radiation from the one or more reference radiation outputs is less than the inspection width.

17. The inspection apparatus of claim 1 wherein the inspection collector apparatus is adapted to collect inspection radiation scattered at one or more angles other than 180°.

18. A method of inspecting a sample which comprises the steps of:

generating superbroad inspection radiation having a frequency spectrum with an inspection width and reference radiation;

applying the inspection radiation to the sample;

collecting inspection radiation which is scattered by the sample;

detecting a plurality of coherent interferences between radiation from the reference radiation and the scattered inspection radiation;

wherein the width of the frequency spectrum of the radiation from the scattered inspection radiation and the width of the frequency spectrum of the radiation from the reference radiation satisfy one of the following:

the width of the frequency spectrum of the radiation from the scattered inspection radiation is substantially the same as the inspection width and the width of the frequency spectrum of the radiation from the reference radiation is less than the inspection width; or the width of the frequency spectrum of the radiation from the scattered inspection radiation is less than the inspection width and the width of the frequency spectrum of the radiation from the reference radiation is substantially the same as the inspection width; or the width of the frequency spectrum of the radiation from the scattered inspection radiation is less than the inspection width and the width of the frequency spectrum of the radiation from the reference radiation is less than the inspection width.

19. The method of claim 18 which further comprises the step of fourier analyzing the output from the step of detecting to provide a spatial image of a portion of the sample.

* * * * *